United States Patent
Ha et al.

(10) Patent No.: US 11,633,708 B2
(45) Date of Patent: Apr. 25, 2023

(54) DIELECTRIC BARRIER DISCHARGE PLASMA REACTOR FOR NON-OXIDATIVE COUPLING OF METHANE HAVING A CONTROLLED GAP DISTANCE BETWEEN DIELECTRIC PARTICLES AND REGENERATION METHOD OF DEACTIVATED BED IN THE SAME

(71) Applicant: Industry-University Cooperation Foundation Sogang University, Seoul (KR)

(72) Inventors: Kyoung-Su Ha, Hanam-si (KR); Juchan Kim, Daegu (KR); Jinwon Lee, Seoul (KR); Jaekwon Jeoung, Seoul (KR)

(73) Assignee: Industry-University Cooperation Foundation Sogang University, Seoul (KR)

( * ) Notice: Subject to any disclaimer, the term of this patent is extended or adjusted under 35 U.S.C. 154(b) by 74 days.

(21) Appl. No.: 16/663,782

(22) Filed: Oct. 25, 2019

(65) Prior Publication Data
US 2020/0129952 A1 Apr. 30, 2020

(30) Foreign Application Priority Data

Oct. 25, 2018 (KR) .................. 10-2018-0128517
Oct. 25, 2018 (KR) .................. 10-2018-0128518

(51) Int. Cl.
*B01J 19/08* (2006.01)
*H05H 1/24* (2006.01)
*C07C 2/82* (2006.01)

(52) U.S. Cl.
CPC .............. *B01J 19/088* (2013.01); *C07C 2/82* (2013.01); *H05H 1/2406* (2013.01); *B01J 2219/0894* (2013.01); *H05H 1/2418* (2021.05)

(58) Field of Classification Search
CPC .............. B01J 19/088; B01J 2219/0894; B01J 2219/0809; B01J 2219/0896;
(Continued)

(56) References Cited

U.S. PATENT DOCUMENTS

| 2003/0157000 A1* | 8/2003 | Janssen | ................ H05H 1/46 422/139 |
| 2004/0148860 A1 | 8/2004 | Fletcher | |
| 2009/0324443 A1* | 12/2009 | Whitehead | ............. B01D 53/32 422/4 |

FOREIGN PATENT DOCUMENTS

| JP | H 08-38881 | 2/1996 |
| KR | 10-0561166 B1 | 3/2006 |

(Continued)

OTHER PUBLICATIONS

"Effect of particle size on Co2 reduction and discharge characteristics in a packed bed plasma reactor", Chemical Engineering Journal, 293 (2016) 55-67 (Year: 2016).*

(Continued)

*Primary Examiner* — Xiuyu Tai
(74) *Attorney, Agent, or Firm* — Daly Crowley Mofford & Durkee, LLP

(57) ABSTRACT

Provided are a dielectric barrier discharge (DBD) plasma reactor including dielectric particles in a packed-bed in a discharge zone, e.g., a DBD plasma reactor for non-oxidative coupling of methane in which an average gap distance between dielectric particles in the packed-bed is adjusted to improve methane conversion and/or product selectivity; a method of regenerating dielectric particles including removing coke, which sis produced by side reactions, from the dielectric particles deactivated by the coke by using a low temperature plasma in an oxidizing atmosphere in the reactor; a method of manufacturing $C_{2+}$ hydrocarbons, the method including converting methane into $C_{2+}$ hydrocar- (Continued)

bons including ethylene and/or ethane by non-oxidative coupling of methane in the reactor; and a method of manufacturing hydrogen, the method including generating hydrogen from methane by non-oxidative coupling of methane in the reactor.

7 Claims, 15 Drawing Sheets

(58) Field of Classification Search
CPC ........ B01J 2219/0828; B01J 2219/0841; B01J 2219/0875; B01J 2219/0892; C07C 2/82; H05H 1/2406; H05H 1/2418; H05H 1/46; B01D 2259/818; B01D 2257/708; B01D 53/32; B01D 2257/404; H01J 37/32009
See application file for complete search history.

(56) References Cited

FOREIGN PATENT DOCUMENTS

| | | |
|---|---|---|
| KR | 10-2012-0134420 A | 12/2012 |
| KR | 2015-0098129 | 8/2015 |

OTHER PUBLICATIONS

Korean Office Action dated Dec. 22, 2021 for Korean Application No. KR1020180128517; 5 pages.
Korean Notice of Allowance/Written Decision on Registration (with Machine English Translation from Espacenet.com) dated Jun. 14, 2022 for Korean Application No. 10-2018-0128517; 7 Pages.

* cited by examiner

DIELECTRIC BARRIER DISCHARGE PLASMA REACTOR FOR NON-OXIDATIVE COUPLING OF METHANE HAVING A CONTROLLED GAP DISTANCE BETWEEN DIELECTRIC PARTICLES AND REGENERATION METHOD OF DEACTIVATED BED IN THE SAME

TECHNICAL FIELD

The present invention relates to: a dielectric barrier discharge plasma reactor including dielectric particles in a bed packed in a discharge zone, e.g., a dielectric barrier discharge plasma reactor for non-oxidative coupling of methane in which a mean value of gap distance between the dielectric particles in the packed-bed is adjusted to improve methane conversion and/or product selectivity; a method of regenerating dielectric particles by removing coke, which is produced by side reactions, from the dielectric particles deactivated by the coke by using a low temperature plasma in an oxidizing atmosphere in the reactor; a method of manufacturing $C_{2+}$ hydrocarbons, the method including converting methane into $C_{2+}$ hydrocarbons including ethylene and/or ethane by non-oxidative coupling of methane in the reactor; and a method of manufacturing hydrogen, the method including generating hydrogen from methane by non-oxidative coupling of methane in the reactor.

BACKGROUND ART

Traditionally, ethylene is obtained by refining petroleum naphtha in the petrochemical industry, and acetylene is obtained by a high temperature pyrolysis of coal or natural gas. However, petroleum has less reserves than gas resources such as natural gas and shale gas and oil price fluctuates more unstably. Although coal reserves are larger and more versatile than petroleum, the use of coal is limited due to excessive costs and energy for pretreatment and emission of a large amount of greenhouse gases emitted during an application process thereof. Thus, research has been conducted to use natural gas resources that are fossil fuels having abundant reserves and causing less environmental problems.

The conversion of methane into mover valuable hydrocarbons and fuels is one of the most important technologies since methane is a primary component of natural gas resources. Considerable research efforts have been made to utilize the abundant reservoirs of natural gas by using efficient catalysts and various conversion technologies. For economic reasons, relatively large-sized gas fields have been developed and used for gas-to-liquids, methanol-to-olefin, methanol synthesis, dimethyl ether synthesis, and the like. These technologies are involved with energy intensive steps such as gasification and reforming, and they are generally conducted at a very high temperature. These severe reaction conditions may limit the choice of reactor materials and reaction catalysts. This situation makes it difficult to reach optimal reaction conditions and prepare or operate the best design. Regarding typical non-oxidative coupling reactions of methane to produce C2 compounds, those reactions in conventional thermochemical reactor usually require a very high temperature (over 1,000° C.) to thermally activate C—H bonds to produce methyl radicals. Among them, BASF process uses pyrolysis, while Huels arc process utilizes high temperature arc plasma to activate and couple methane molecules. Even with catalysts and oxygen co-reactants, a temperature of at least 800° C. is required to produce C2 compounds (mostly ethylene and ethane) through the oxidative coupling of methane (OCM), one of the most representative and well-studied conversion technologies. Although this technology shows relatively high yields of C2 compounds, problems such as high exothermicity of OCM reaction and separation burden due to air separation unit for the supply of pure oxygen and the production of pure products may occur.

To avoid such energy-intensive conversions, costly separation units, and high operating cost, non-traditional conversion technologies using various energy sources minimizing external thermal heat flows have been recently drawing much attention. Among them, a non-thermal plasma technology has been intensively and extensively studied recently since it directly and efficiently utilizes accelerated electrons and ions to activate the C—H bonds of methane molecules at relatively low temperature without heating all the reaction medium in the bed up to an elevated temperature. Under the non-thermal plasma reaction system, electron temperature is increased up to 20000 K and the electrons mainly contribute to the reaction. However, the temperature of the bulk including positively charged ions and neutral molecules is close to room temperature. For these reasons, this type of plasma is regarded as the non-thermal, non-equilibrium plasma (i.e., electron temperature>>gas temperature).

For example, the first ozone generation by a non-thermal dielectric barrier discharge (DBD) plasma method was introduced in the middle of $19^{th}$ century. The ozone has been commercially produced by using the similar DBD technique nowadays. Norsic et al. researched methanol oxidation by a DBD plasma combined with $MnO_2$—CuO-based catalysts. The removal of $NO_x$ compounds using a non-thermal plasma method has been studied. Also, the removal of $SO_x$ and VOC has been studied by DBD plasma and non-thermal plasma techniques. Recently, the conversion methods by plasma have been reported to produce valuable products. Ozkan et al., Rahmani et al., and Yap et al. introduced a dry reforming method of methane to produce synthetic gas and hydrogen by using DBD plasma. Wang et al. reported a steam-enhanced dry reforming technique in a DBD plasma reactor. Liu et al. researched a low temperature plasma to produce light hydrocarbons with a catalyst and reported non-oxidative reaction pathways including catalytic conversion. They explained that methane could be converted into methyl radical by reacting with hydrogen radical or electron having over 10 eV, followed by subsequent reactions such as coupling reactions. Nozaki et al. performed optical emission spectroscopic measurement for rotational and vibrational state of excited $CH(A^2\Delta)$ radical in a packed-bed dielectric barrier discharge reactor. They confirmed that the rotational equilibrium of excited $CH(A^2\Delta)$ is sufficiently established within radioactive lifetime (2-3 ns). Similar approach with $TiO_2$ and $MgO/Al_2O_3$ catalyst pellets ranging from 0.25 to 1.75 mm was published more recently, and they argued that the smaller catalyst pellets seemed to stabilize the radical intermediates and enhance the surface interaction between the reacting species. They added that this led to increased methane conversion and hydrocarbon selectivity as well. It was pointed out that the pellets refract the electric field, making it non-uniform and stronger than the externally applied field by a factor of 10 to 250. According to related art documents, when the packed dielectric particles are polarized due to an applied voltage, a local electric field is enhanced near at contact points between beads. Furthermore, electron energies were increased, which produce more energetic electrons and reactive species for the reaction. It leads to higher reactant conversion compared to an unpacked DBD reactor. Regarding the packed-bed reactor with non-thermal plasma, Butterworth et al. pointed out that the small particles in the bed increased the density of contact points initiating discharges, the interfacial area between solid and plasma for heterogeneous catalytic reaction, and the volume fraction of gas-plasma contacts. It was also added that the surface discharge might become increasingly dominant over micro-discharges in the packed-bed with small particles. Disadvantages were pointed out that smaller particles may inhibit the formation of a discharge in the void spaces, increase pressure drop through the bed, and increase the loss rate of reactive species and electrons.

DESCRIPTION OF EMBODIMENTS

Technical Problem

An object of the present invention is to provide a dielectric barrier discharge plasma reactor including a bed packed with dielectric particles whose material, size, shape, porosity, or the like is adjusted to achieve desired reaction results (methane conversion, product selectivity, and/or suppression of coke formation) by analyzing effects of the dielectric particles on non-oxidative coupling of methane performed in the dielectric barrier discharge plasma reactor.

Another object of the present invention is to provide a method of removing carbon-containing by-products such as carbon deposition and hydrocarbons produced in a reaction bed during reaction by using a dielectric barrier discharge plasma that is a low temperature plasma.

Another object of the present invention is to provide a method of removing carbon-containing by-products such as carbon deposition and hydrocarbons produced during the reaction while maintaining a structure and an intrinsic crystal structure of particles by using a dielectric barrier discharge plasma that is a low temperature plasma.

Solution to Problem

It is a first aspect of the present invention to provide a dielectric barrier discharge (DBD) plasma reactor including dielectric particles in a packed-bed in a discharge zone.

It is a second aspect of the present invention to provide a method of regenerating the dielectric particles comprising treating the dielectric particles deactivated by coke with low temperature plasma under an oxidizing atmosphere in the DBD plasma reactor according to the first aspect to remove the coke produced by side reactions.

It is a third aspect of the present invention to provide a method of manufacturing $C_{2+}$ hydrocarbons, the method including a first step of converting methane into $C_{2+}$ hydrocarbons including ethylene and/or ethane by non-oxidative coupling of methane in the reactor according to the first aspect.

It is a fourth aspect of the present invention to provide a method of manufacturing hydrogen, the method including a first step of generating hydrogen from methane by non-oxidative coupling of methane in the reactor according to the first aspect.

Hereinafter, the present invention will be described in detail.

The present inventors have conducted coupling reactions in a dielectric barrier discharge (DBD) plasma bed near atmospheric pressure and room temperature using a DBD plasma reactor for non-oxidative coupling of methane employing dielectric materials such as ordered mesoporous silica (KIT-6), sea sand silica, and $\alpha$-$Al_2O_3$. This non-catalytic reaction system may successfully activate C—H bonds to produce methyl radicals and light hydrocarbons without additional thermal energy and oxidant molecules. In addition, a composition ratio of ethane, ethylene, and acetylene may be controlled by appropriately adjusting size or gap distance of the dielectric particles. It was experimentally found that the gap distance between dielectric particles may be determined by sizes thereof and the effects of the gap distance were found significant on the conversion rate and selectivity. The existence of maximum conversion rate at a specific gap distance was experimentally observed and could be described, and based on findings that hydrocarbon selectivity may be controlled by adjusting particle size regardless of type and porosity of materials of dielectric particles, a new concept of micro-electrodes as illustrated in FIG. 1 was developed.

Meanwhile, in the case of highly porous dielectric particles, the amount of carbon deposition was considerable. The carbon species were also deposited inside the pores. In addition, as the size of the dielectric particles increased, the intensity of micro-discharges increased, thereby increasing the amount of carbon deposition. As a result of TG/DTA analysis, it was confirmed that two major carbon species were deposited. From X-ray diffraction (XRD) analysis results, most of carbon species were found amorphous. In addition, through Fourier-transform infrared spectroscopy (FT-IR), the carbon species was classified as carbon deposition having long-chain hydrocarbons.

To solve the above-described problems, experiments were performed using a low temperature dielectric barrier discharge plasma reactor system that produces mostly C2 compounds, such as ethane, ethylene, and acetylene, and hydrogen from methane by dimerization and dehydrogenation, and it has been found that a mixture of carbon deposition inevitably produced by side reactions during the reaction may be removed by the same plasma as that used in the reaction according to the present invention. Therefore, the present inventors have designed a method of regenerating a bed that has considerably undergone deactivation by the reaction in situ without removing a packing material, thereby completing the present invention.

Also, to solve the above-described problems, according to the present invention, it has been found that structural stability of a packing material is not influenced by oxygen-free methane coupling reaction and regeneration reaction of the packing material by using a DBD plasma, while a regeneration reaction using a muffle furnace affects the structural stability of the packing material (Example 7, Example 8, and Table 8). The present invention is based thereon.

A DBD plasma reactor according to an embodiment of the present invention may be designed to perform non-oxidative coupling of methane in a plasma bed including dielectric particles. In this case, during the non-oxidative coupling of methane, methyl radicals and C2-C4 light hydrocarbons may be directly produced by activating C—H bonds without additional thermal energy and oxidant molecules. The dielectric particles may serve as a catalyst for non-oxidative coupling of methane. For example, the dielectric particles may further carry a catalytic active component for non-oxidative coupling of methane.

That is, as a result of experiments for the effects of particle size, far below the conventional pellet size (about 1 mm to about 10 mm) in a dielectric barrier discharge (DBD) plasma reactor for non-oxidative coupling of methane, the present inventors have found that (1) the methane conversion rate is not monotonically increased as the size of the dielectric particles is decreased; (2) the conversion rate is maximized when the size of the dielectric particles is in a microscale range (e.g., 200 µm or less); (3) hydrocarbon selectivity is controlled by adjusting the size of particles without catalysts, regardless of the type and porosity of materials, through experiments with different sizes of particles; and (4) performance seemed to be influenced by a dielectric constant, morphology of particles, and the like. The present invention is based thereon.

Furthermore, the gap distance between dielectric particles is determined by the size of particles. A gap distance at a maximum conversion rate was observed by experiments, and this result was further analyzed by employing the concept of micro-electrodes. Thus, a minimum threshold electric potential difference for the maximum conversion rate may be calculated by a modified Paschen's equation represented by Equation 1.

Therefore, the present invention is provided to explain a direct non-catalytic conversion mechanism of methane into C2-C4 hydrocarbons at room temperature and the relationship between the maximum methane conversion rate and the gap distance using the newly developed micro-electrode concept.

FIG. 1 illustrates (1) a local microelectric field between particles and (2) propagation of streamers and micro-discharges between polarized micro-electrodes. In FIG. 1, micro-electrodes are induced by an external electric field between packed dielectric particles. Due to the high voltage and the dielectric barrier, streamers and micro-discharges are generated. When these streamers and micro-discharges reach the top surface of a particle, the top surface is positively charged due to polarization. At this moment, the bottom surface is negatively charged. The top and bottom surfaces turn out to be anode-like and cathode-like surfaces, respectively. This phenomenon starts from the particles near an external cathode and consecutively takes place from particle to particle to a direction toward an opposite electrode. When the streamers surround the dielectric particles, electrons are seeded from the bottom surfaces of the particles since the intensity of local electric field is enhanced due to photoionization. The seeded electrons cause another avalanche and launch new streamers. At that moment, nitrogen and methane molecules collide with accelerated electrons and consequently positively charged ions are generated. Under the enhanced electric field, the generated positive ions are accelerated to the cathode-like surface and collide with the surface. This collision produces secondary electrons to sustain the streamers. Thus, the induced local electric field and the induced charged surfaces of particles may be regarded as a microelectric field and micro-electrodes, respectively. By following this scheme, the Paschen's equation in a modified form may successfully be applied to the induced local microelectric field between adjacent particles as if those induced charged surfaces are external electrodes (denoted micro-cathode and micro-anode in FIG. 1).

In addition, through experimental observation of dielectric particles classified into three groups in terms of particle size (small-sized (S), middle-sized (M), and large-sized (L); 0<S<53<M<100<L<150 µm), it was found that the maximum conversion rate of methane may be obtained by packing M particles. A gap distance between M particles was in the range of 4 µm to 5 µm as shown in FIG. 3 and Table 2. A lower breakdown voltage leads to a higher conversion rate. Based on these two findings, experimental results may successfully be explained by applying the Paschen's equation and the concept of micro-electrodes to the gap between charged dielectric particles. Thus, the present invention suggests a modified Paschen's equation represented by Equation 1 below by combining the original Paschen's equation and the concept of micro-electrodes.

$$\ln\left(1 + \frac{1}{\gamma}\right) = A \cdot pd_{micro} \cdot \exp\left(-\frac{Bpd_{micro}}{\Delta V_{B,micro}}\right) \qquad \text{Equation 1}$$

or $$\Delta V_{B,micro} = \frac{Bpd_{micro}}{\ln(pd_{micro}) + \ln\left[\frac{A}{\ln\left(1 + \frac{1}{\gamma}\right)}\right]}$$

Based on the concept of micro-electrodes illustrated in FIG. 1, a minimum threshold electric potential difference between the dielectric particles may successfully be estimated, where the conversion rate is maximized. Thus, to find the equation for the minimum threshold electric potential difference, a differentiation of potential difference with respect to the gap distance was performed. The resulting equation is represented by Equation 2 below.

$$d_{min,micro} = \frac{e}{Ap} \cdot \ln\left(1 + \frac{1}{\gamma}\right) \text{(where, } e = \exp(1)) \qquad \text{Equation 2}$$

or $$\gamma = \frac{1}{\exp\left(\frac{Apd_{min,micro}}{e}\right) - 1}$$

In Equations 1 and 2, $\Delta V_{B,micro}$: threshold electric potential difference between micro-electrodes to initiate plasma discharges, $d_{micro}$: gap distance between two micro-electrodes, $d_{min,micro}$: minimum gap distance between two micro-electrodes, $\gamma$: second Townsend ionization coefficient; secondary electron emission coefficient of micro-cathode, $\sigma$: collision cross-sectional area of the gas molecule, $E_{micro}$: electric field strength between two micro-electrodes, $U_i$: ionization potential of the gas molecule, $k_B$: Boltzmann constant, T: gas temperature, p: gas pressure, A: ionization characteristic constant of the gas molecule (Equivalent to $\sigma/k_B T$), and B: ionization constant of the gas molecule (Equivalent to $U_i \sigma/k_B T$).

Therefore, the gap distance between dielectric particles provided in a discharge zone may be adjusted to have a low breakdown voltage in the DBD plasma reactor, and an average gap distance between the dielectric particles may be in the range of 1 µm to 20 µm. Through experiments, the gap distance between the dielectric particles may be determined by sizes thereof, and an average particle diameter of the dielectric particles may be in a microscale range of 10 µm to 200 µm.

In addition, a method of regenerating the DBD plasma reactor and/or dielectric particles according to an aspect of the present invention may be explained using the concept of micro-electrodes as follows.

(1) Micro-electrodes are induced between packed dielectric particles by an external electric field, and a local microelectric field is induced between the dielectric particles.

(2) Streamers and micro-discharges propagate between polarized micro-electrodes due to an externally applied high voltage and the dielectric barrier.

(3) The streamers and micro-discharges reaching the top surface of a particle cause the top surface to be positively charged due to polarization, and then the bottom surface of the particle to be negatively charged at the same time, the top surface and the bottom surface turning into an anode-like surface and a cathode-like surface, respectively. This phenomenon starts from the particles near the external cathode and consecutively takes place from particle to particle to a direction toward an opposite electrode.

(4) When the streamers surround the dielectric particles, an intensity of a local electric field is enhanced due to photoionization, and thus electrons are seeded from the bottom surfaces of the particles, and the seed electrons cause another avalanche and launch new streamers. At that moment, nitrogen and methane molecules collide with the accelerated electrons and positively charged ions are generated. Under the enhanced electric field, the generated positive ions are accelerated to the cathode-like surface and collide with the surface, and this collision produces secondary electrons to sustain the streamers.

(5) The induced local electric field and the induced charged surface of particles are regarded as a microelectric field and micro-electrodes, respectively. The modified Paschen's equation represented by Equation 1 is applied to the induced local microelectric field between adjacent particles as if those induced charged surfaces are a micro-cathode and a micro-anode.

Meanwhile, the dielectric barrier discharge (DBD) plasma reactor including dielectric particles in the discharge zone according to an aspect of the present invention is designed to remove coke, which is produced on the dielectric particles by side reactions, by plasma treatment in an oxidizing atmosphere. For example, the non-oxidative coupling of methane performed in the DBD plasma reactor is a reaction of synthesizing ethane, ethylene, acetylene, hydrogen, and the like by dimerizing methane at room temperature. By the reaction, a small amount of a gas mixture of C3 and C4 hydrocarbons is obtained and the carbon deposition and a mixture of tar-like hydrocarbons are formed in the bed, thereby decreasing plasma conversion.

Thus, the DBD plasma reactor according to an aspect of the present invention may be designed to remove coke, which is inevitably produced by side reactions occurring in the DBD plasma reactor, by using the same type of plasma as that used in the reaction while supplying an oxygen-containing mixture, instead of the reaction mixture, during a regeneration process.

In addition, the method of regenerating dielectric particles according to an aspect of the present invention is characterized by comprising treating the dielectric particles deactivated by coke with low temperature plasma under an oxidizing atmosphere in the above-described dielectric barrier discharge (DBD) plasma reactor to remove the coke produced by side reactions. The dielectric particles regenerated by the low temperature plasma treatment according to the regeneration method of the present invention may maintain an ordered mesoporous structure of the electric particles before use or an intrinsic crystal structure thereof. Therefore, the DBD plasma reactor and/or regeneration method according to the present invention are effective to regenerate the ordered mesoporous dielectric particles.

In this regard, the coke removed by using the low temperature plasma may be an amorphous carbonaceous material and/or a graphitic carbonaceous material.

Thus, in the dielectric barrier discharge plasma reactor for non-oxidative coupling of methane according to the present invention, an average gap distance between dielectric particles in the packed-bed may be adjusted in the range of 1 μm to 20 μm, preferably, 4 μm to 5 μm to improve the methane conversion rate in non-catalytic conversion of methane into $C_{2+}$ hydrocarbons by non-oxidative coupling. As a result of applying the modified Paschen's equation represented by Equation 1 or 2 based on the concept of micro-electrodes, it was experimentally observed that particles having a gap distance of 4 μm to 5 μm exhibit the lowest breakdown voltage, and the methane conversion rate increases thereby.

At an operating temperature of the dielectric barrier discharge plasma reactor for non-oxidative coupling of methane, dielectric particles packed in the bed may not exhibit a catalytic activity for the non-oxidative coupling of methane.

The dielectric barrier discharge plasma reactor for non-oxidative coupling of methane may activate C—H bonds without additional thermal energy and oxidant molecules to produce methyl radicals and directly produce C2-C4 light hydrocarbons.

In this case, the gap distance between dielectric particles may be determined by the size of particles. For example, after sampling a plurality of scanning electron microscope (SEM) images of the particles (FIG. 2), the gap distance between the particles may be identified by direct sampling, counting, and statistically processing the distances between the particles.

Thus, it is possible to design a gap distance between dielectric particles to obtain desired methane conversion rate and C2 selectivity and pack the dielectric particles designed to have the size providing the designed gap distance in the bed.

An average particle diameter of the dielectric particles packed in the bed may be adjusted to 200 μm or less, preferably, in the range of 50 μm to 100 μm. In the SEM analysis, the average gap distance between particles having a particle diameter of 50 μm to 100 μm was in the range of 4 μm to 5 μm, and as a result of applying the modified Paschen's equation represented by Equation 1 or 2 based on the concept of micro-electrodes, it was experimentally observed that the lowest breakdown voltage was obtained when the gap distance between particles was in the range of 4 μm to 5 μm, leading to a high methane conversion rate.

In addition, in the dielectric barrier discharge plasma reactor for non-oxidative coupling of methane according to the present invention, the bed may be packed with dielectric particles having an adjusted size to inhibit formation of coke on the dielectric particles during the reaction or to adjust the timing of removing coke formed on the dielectric particles during the reaction.

In the case of highly porous dielectric particles, the amount of carbon deposition was considerable. The carbon species seemed to be deposited inside the pores. In terms of the yield of hydrocarbons, the performance in $\alpha\text{-}Al_2O_3$-packed bed was very high, whereas the least amount of coke was produced in sea sand-packed bed. As the size of particles increased, the dehydrogenation seemed to be accelerated by an increased intensity of micro-discharges, and the amount of carbon deposition was increased accordingly.

Thus, in consideration that the amount of carbon deposition increases due to accelerated dehydrogenation caused by an increase in the intensity of micro-discharges as the particle size increases; and/or the amount of carbon deposition varies according to porosity in the case of porous dielectric particles, it is possible to predict when to remove coke formed on the dielectric particles.

Meanwhile, the method of producing $C_{2+}$ hydrocarbons according to the present invention includes converting methane into $C_{2+}$ hydrocarbons including ethylene and/or ethane by non-oxidative coupling of methane in the above-described dielectric barrier discharge plasma reactor for non-oxidative coupling of methane according to the present invention.

The $C_{2+}$ hydrocarbons may be used as raw materials to be converted into high value added chemicals and high energy fuels.

The above-described dielectric barrier discharge plasma reactor for non-oxidative coupling of methane according to the present invention may control hydrocarbon selectivity by adjusting the size or the gap distance of the dielectric particles regardless of the type and porosity of materials of the dielectric particles packed in the bed. For example, the composition ratio of ethane, ethylene, and acetylene may be controlled by adjusting the size of the gap distance of dielectric particles packed in the bed or the gap distance.

For example, a method of producing $C_{2+}$ hydrocarbons according to an embodiment of the present invention includes:

a first step of converting methane into $C_{2+}$ hydrocarbons including ethylene and/or ethane by non-oxidative coupling of methane in a dielectric barrier discharge (DBD) plasma reactor including dielectric particles packed in a discharge zone; and a second step of treating the dielectric particles deactivated by coke with low temperature plasma under an oxidizing atmosphere in the DBD plasma reactor to remove the coke produced by side reactions.

The $C_{2+}$ hydrocarbons may be used as raw materials to be converted into high value added chemicals and high energy fuels.

The first step and the second step may be repeated once or more. Since the DBD plasma reactor uses a low temperature plasma as an energy source, additional heat supply is not required to perform the first step and/or the second step.

Although the first step and the second step may be performed in different DBD plasma reactors, they may preferably be performed in the same DBD plasma reactor. This is because the mixture of carbon deposition inevitably produced by side reactions during the reaction performed in the DBD plasma reactor may be removed by using the same type of plasma as that used in the reaction, and the oxygen-containing mixture is used in the regeneration process instead of the methane-containing reaction mixture. That is, according to the present invention, the carbon-containing deposition may be activated and decomposed using the DBD plasma by injecting the oxygen-containing mixture (e.g., air) instead of the methane mixture for regeneration.

Since the non-oxidative coupling of methane is accompanied by dehydrogenation, the dielectric barrier discharge plasma reactor for non-oxidative coupling of methane according to the present invention may also be applied to production of hydrogen from methane.

Therefore, a method of manufacturing hydrogen from methane by non-oxidative coupling of methane according to an embodiment of the present invention includes:

a first step of generating hydrogen from methane through non-oxidative coupling of methane in a dielectric barrier discharge (DBD) plasma reactor including dielectric particles in a discharge zone; and a second step of treating the dielectric particles deactivated by coke with low temperature plasma under an oxidizing atmosphere in the DBD plasma reactor to remove the coke produced by side reactions.

The first step and the second step may be repeated once or more. In addition, the first step and the second step may be performed in the same DBD plasma reactor. Since the DBD plasma reactor uses a low temperature plasma as an energy source, additional heat supply is not required to perform the first step and/or the second step.

Advantageous Effects of Disclosure

The present invention may provide a dielectric barrier discharge plasma reactor including a bed packed with dielectric particles whose material, size, shape, porosity, or the like is adjusted to achieve desired reaction results (methane conversion, product selectivity, and/or coke formation suppression) by analyzing effects of the dielectric particles on non-oxidative coupling of methane performed in the dielectric barrier discharge plasma reactor. In addition, according to the present invention, carbon-containing by-products such as carbon deposition and hydrocarbons produced in a reaction bed during the reaction may be removed by using a dielectric barrier discharge plasma that is a low temperature plasma. Particularly, crystalline coke produced as a by-product during a high temperature coupling process may be inhibited or suppressed, and a low temperature coupling process and/or a low temperature regenerating process may be realized by using a low temperature plasma, thereby improving energy efficiency.

MODE OF DISCLOSURE

Hereinafter, the present invention will be described in more detail with reference to the following examples. However, these examples are for illustrative purposes only and are not intended to limit the scope of the present invention.

Preparation Example 1: Preparation of Materials

The $\alpha\text{-}Al_2O_3$ was prepared by thermal treatment of $\gamma\text{-}Al_2O_3$(Sigma-Aldrich, USA) at 1000° C. for 8 hours.

Sea sand was purchased from Fisher Chemical, USA.

Ordered mesoporous silica (KIT-6) was prepared in the following method.

6 g of a triblock copolymer P123 ($EO_{20}PO_{70}EO_{20}$, MW=5800 g/mol, Sigma-Aldrich, USA) was dissolved in 217.64 g of deionized water and 11.16 g of HCl (37%, Sigma-Aldrich, USA) at 35° C. while agitating to prepare a homogenous solution. Then, 6 g of 1-butanol (Sigma-Aldrich, USA) was added to the mixture and stirred for 2 hours. 12.77 g of a silica precursor, tetraethoxy silane (Alfa Aesar, USA) was slowly added to the mixture and stirred for 24 hours. This mixture was added to a polypropylene bottle and hydrothermally treated at 100° C. for 24 hours and washed three times with deionized water and ethanol. Subsequently, the washed sample was placed in an oven and dried at 110° C. for 24 hours. The dried sample was calcined at 550° C. for 5 hours.

All materials were separated to three groups (S, M and L; 0<S<53<M<100<L<150 m) in terms of particle size by using stainless steel sieves.

Experimental Example 1: Analysis of Characteristics of Materials

Figure 2:
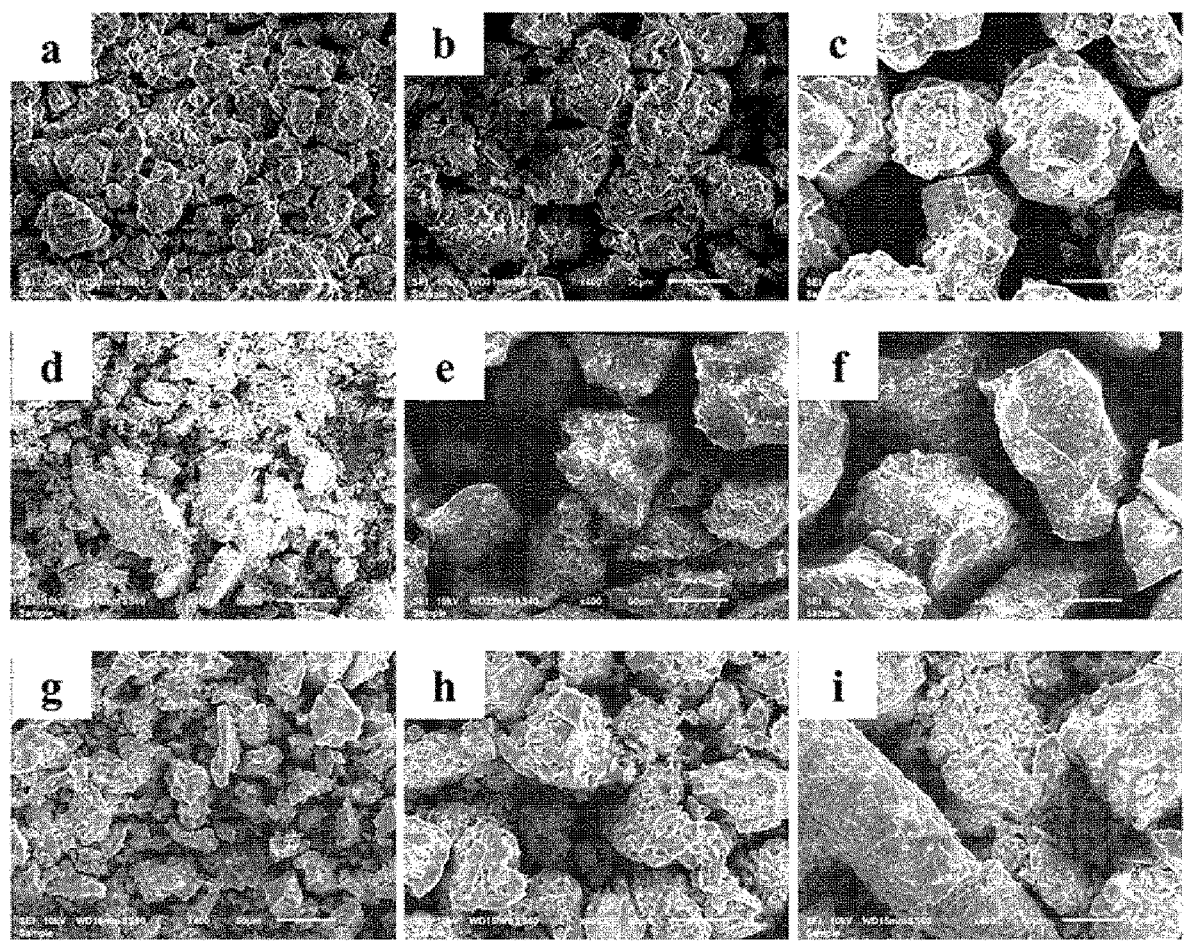
FIG. 2 shows scanning electron microscope (SEM) images of (a) fresh $\alpha$-$Al_2O_3$ (S), (b) fresh $\alpha$-$Al_2O_3$ (M), (c) fresh $\alpha$-$Al_2O_3$ (L), (d) fresh sea sand (S), (e) fresh sea sand (M), (f) fresh sea sand (L), (g) fresh KIT-6 (S), (h) fresh KIT-6 (M), and (i) fresh KIT-6 (L).
Figure 3:
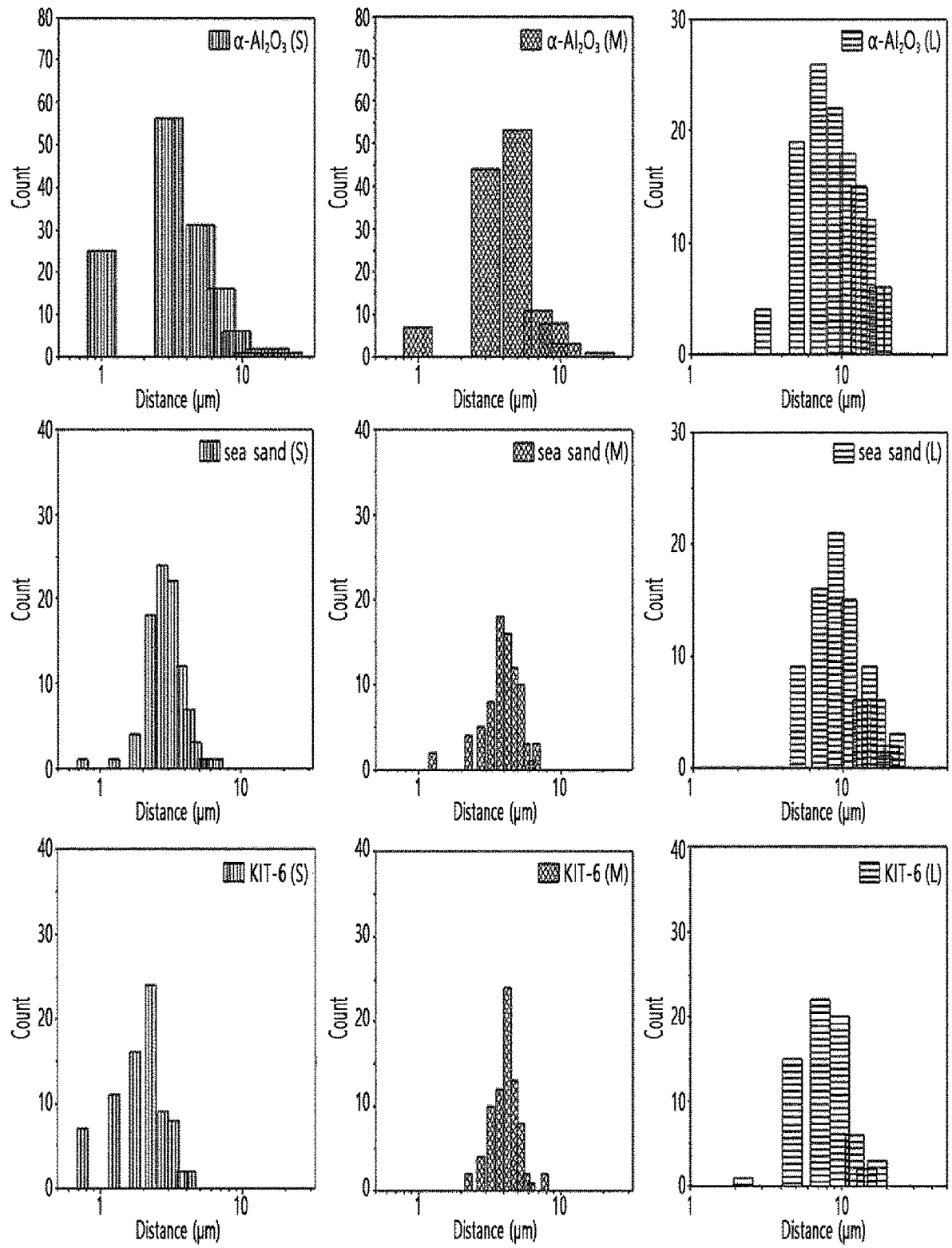
FIG. 3 shows graphs illustrating distributions of gap distance between particles obtained from the SEM images of fresh samples.

For each material prepared in Preparation Example 1, 3 groups with different sizes were prepared and the groups were named S, M, and L as shown in Table 1. SEM images are provided in FIG. 2. Gap size distribution between particles are shown in FIG. 3 and Table 1. In this regard, the gap is significantly related to the particle size. In the case of the $\alpha\text{-}Al_2O_3$ particles, mean values of gap between S, M, and L particles were 4.30 m, 4.73 m, and 9.87 μm, respectively.

In the cases of the sea sand and KIT-6 particles, the gap increases with the particle size. As described above, the particles of each group appeared to have log-normal distribution.

TABLE 1

| Sample | Mean (μm) | Minimum (μm) | Standard deviation (μm) |
| --- | --- | --- | --- |
| $\alpha\text{-}Al_2O_3$ (S) | 4.30 | 0.55 | 3.22 |
| $\alpha\text{-}Al_2O_3$ (M) | 4.73 | 1.12 | 2.37 |
| $\alpha\text{-}Al_2O_3$ (L) | 9.87 | 3.52 | 4.15 |
| sea sand (S) | 3.04 | 0.77 | 0.94 |
| sea sand (M) | 4.10 | 1.05 | 1.09 |
| sea sand (L) | 10.87 | 4.28 | 4.44 |
| KIT-6 (S) | 2.07 | 0.59 | 0.78 |
| KIT-6 (M) | 4.23 | 2.14 | 0.97 |
| KIT-6 (L) | 8.43 | 3.16 | 3.15 |

Example 1: Packed-Bed DBD Plasma Reactor and Activity Test

Figure 4:
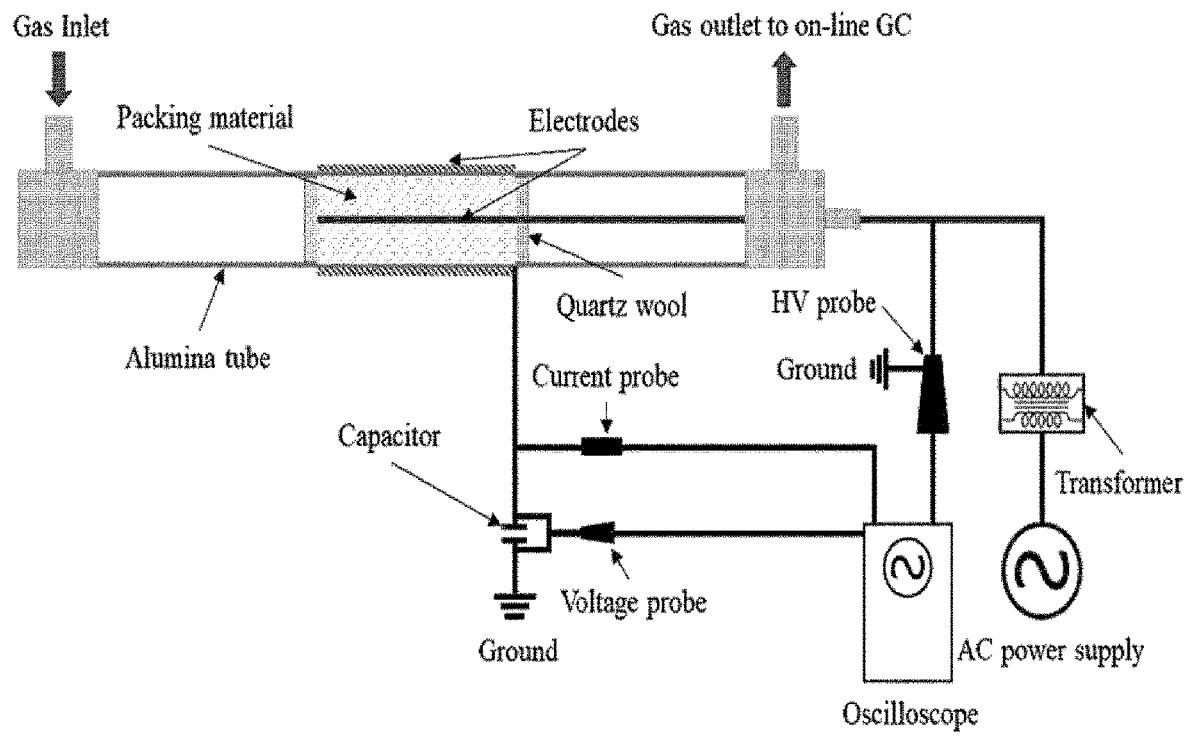
FIG. 4 is a schematic diagram of a bed plasma reactor system.

Non-oxidative methane coupling reaction was conducted in a lab-made packed-bed DBD plasma reactor system (FIG. 4) at atmospheric pressure and near room temperature.

Figure 5:
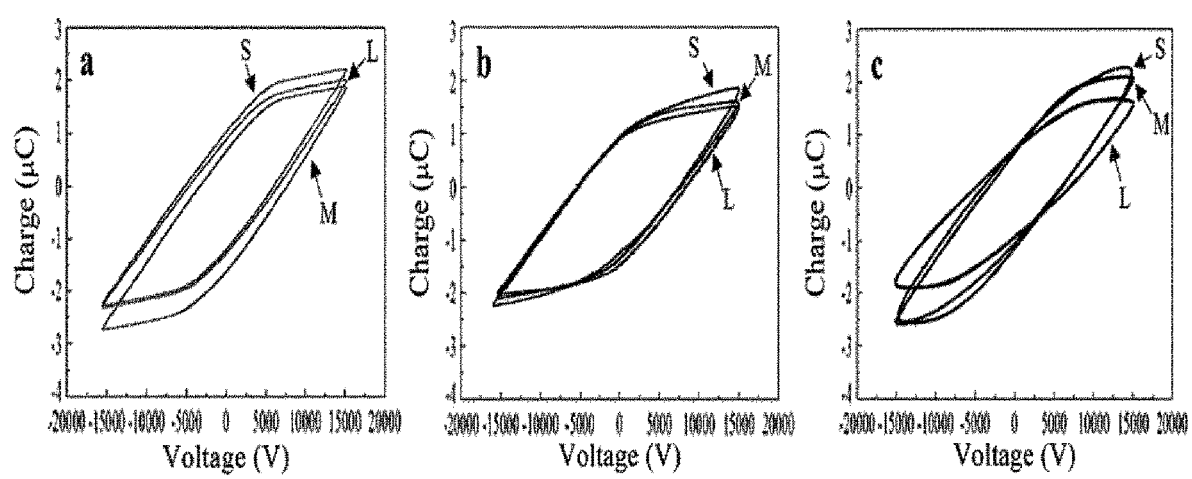
FIG. 5 shows Lissajous curves of measured voltage (V) and charge (Q) of (a) $\alpha$-$Al_2O_3$ samples, (b) sea sand samples, and (c) KIT-6 samples.

A volumetric flow rate of a methane mixture ($CH_4:N_2$=1:1) was 40 standard cubic centimeter per minute (sccm), and a total time for the reaction was 1000 minutes. An alumina tube having an internal diameter of 6 mm and a thickness of 2 mm was used as a dielectric barrier for the plasma bed. A stainless steel rod having a diameter of 3 mm was used as a powered electrode, and a steel wire was used as a ground electrode. A 150 mm-long discharge zone was covered with the ground electrode. A discharge gap between the inner surface of the alumina tube and a high-voltage electrode was 1.5 mm, a volume of the plasma discharge zone was fixed to 3.181 $cm^3$, and a space velocity (SV) based on the volume was set to 754.5 $h^{-1}$. Each dielectric packing material was fully packed in this region. Each dielectric packing material was fully packed in this region. A sinusoidal AC power supply (0-220 V, 60-1000 Hz) was connected to a transformer (0-20 kV, 1000 Hz), and this electrical system continuously applied a high voltage to the plasma bed. The applied voltage and the frequency to the plasma bed were fixed as 15 kV and 1 kHz, respectively. A capacitor with capacitance of 1 μF was connected in series between the plasma bed and the ground. The voltage applied to the plasma bed was measured by employing a high-voltage probe (1000:1, P6015A, Tektronix). The voltage across the 1 µF capacitor was measured by employing a voltage probe (10:1, P6100, Tektronix) connected to each side of the capacitor. A current probe (TCP202, Tektronix) was connected on the ground electrode to evaluate the current profile across the DBD plasma bed. The probes were connected to a digital oscilloscope (TDS 3012C, Tektronix). The accumulated electric charge in the plasma bed was calculated by multiplying the voltage across the capacitor and the capacitance of the capacitor (1 µF). FIG. 5 shows Lissajous curves of measured voltage (V) and charge (Q) of (a) α-$Al_2O_3$ samples, (b) sea sand samples, and (c) KIT-6 samples. Table 2 shows discharge power calculated by Q-V Lissajous method, calculated energy yields of total C2 and unsaturated C2 hydrocarbon products per discharge power, weight of particles in each bed, breakdown voltage in each bed, and calculated average threshold electric potential difference between particles.

During the reaction, the reactor temperature was measured with an IR temperature detector. The temperature at inlet was nearly room temperature and the temperature of the bed was monitored. The maximum temperature was observed in the central region of the reactor as 100° C. The observed temperatures in the other regions were below 100° C. and most were close to room temperature. An external insulation or an oven was used in this reactor system.

An effluent gas from the plasma bed was analyzed by an on-line gas chromatograph (6500GC Young Lin Instrument Co., Korea) employing a Porapak-N and a Molecular Sieve 13× columns connected with a thermal conductivity detector (TCD) and a GS-GasPro column connected with a flame ionization detector (FID). $H_2$, $N_2$, and $CH_4$ in the effluent were detected by using the TCD. $CH_4$, $C_2H_2$, $C_2H_4$, $C_2H_6$, $C_3H_6$, $C_3H_8$, 1-$C_4H_8$, and n-$C_4H_{10}$ in the effluent gas were detected by using the FID. The energy yield (Yi) of product i and the corresponding discharge power was rigorously calculated in Table 2.

TABLE 2

| Sample | Discharge power (W) | $Y_{total\ C2}$ (g/kWh) | $V_{unsaturated\ C2}$ (g/kWh) | Weight of particles (g) | Breakdown voltage [a] (kV) | Threshold ΔV [b] (V) |
|---|---|---|---|---|---|---|
| α-$Al_2O_3$ (S) | 44.1 | 11.26 | 9.21 | 5.09 | 5.56 | 91.4 |
| α-$Al_2O_3$ (M) | 43.5 | 8.61 | 5.98 | 5.06 | 5.53 | 90.9 |
| α-$Al_2O_3$ (L) | 42.5 | 8.11 | 4.27 | 3.77 | 5.60 | 109 |
| sea sand (S) | 43.0 | 7.28 | 5.32 | 5.37 | 6.52 | 84.0 |
| sea sand (M) | 42.0 | 6.98 | 4.56 | 5.27 | 6.49 | 79.0 |
| sea sand (L) | 42.3 | 5.50 | 2.35 | 4.87 | 6.93 | 106 |
| KIT-6 (S) | 39.0 | 4.65 | 3.02 | 1.28 | 4.91 | 143 |
| KIT-6 (M) | 38.5 | 6.83 | 4.32 | 1.00 | 4.56 | 81.5 |
| KIT-6 (L) | 36.1 | 7.66 | 3.62 | 0.91 | 5.95 | 95.8 |

[a] Measured from Q-V curves in FIG. 5.
[b] Threshold electric potential difference (ΔV) between particles to initiate plasma discharges, calculated from Equation 1.

1.1. Activity Tests in DBD Plasma Bed

Figure 6:
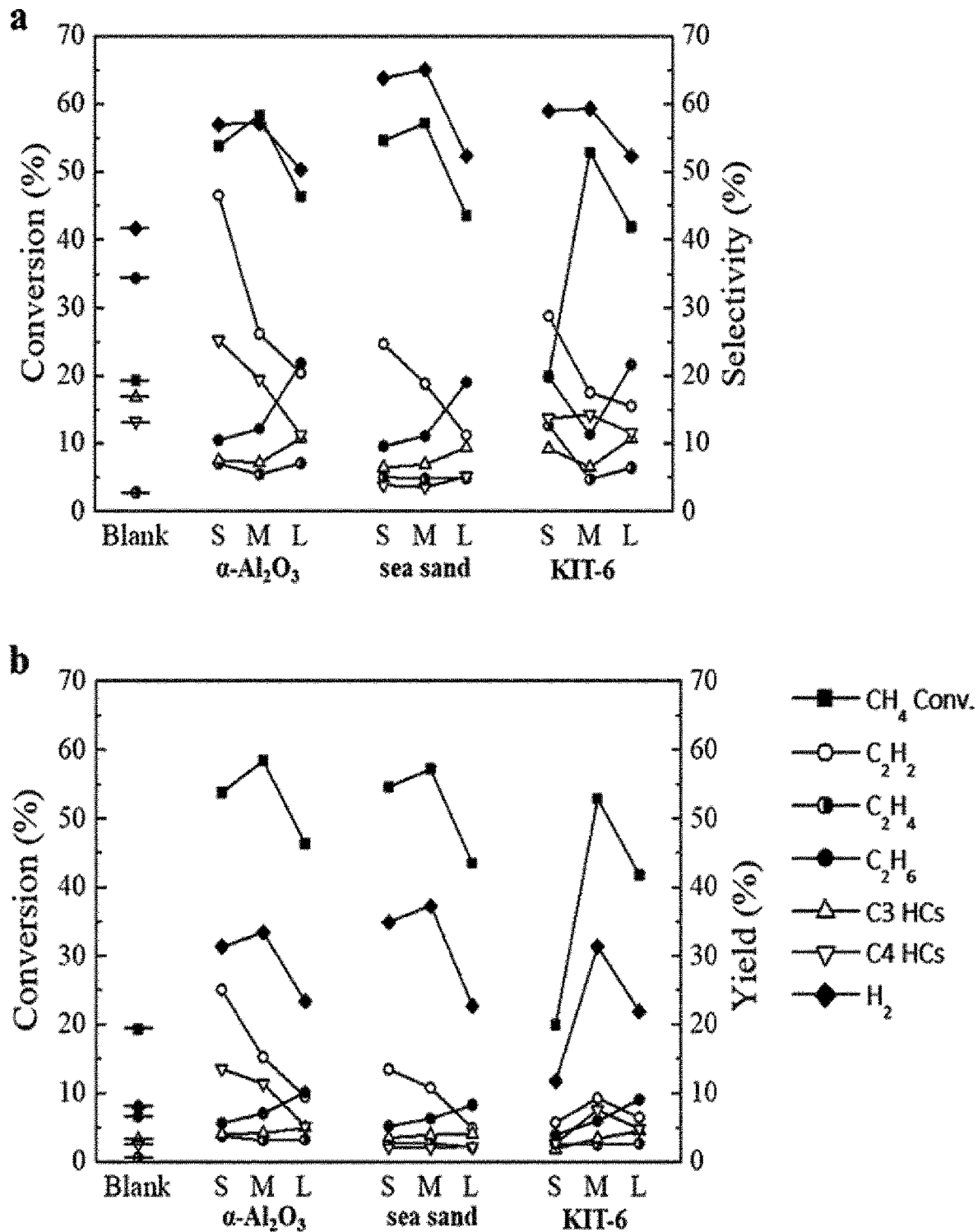
FIG. 6 shows reaction performance of cases without dielectric particles (blank) and with $\alpha$-$Al_2O_3$, sea sand, and KIT-6 at TOS 60 min: (a) of FIG. 6 shows $CH_4$ conversion rates and product selectivities, and (b) of FIG. 6 shows $CH_4$ conversion rates and yields of products.

As shown in FIG. 6, the packed beds showed the higher conversion rate in all the cases than the conversion rate of blank test at the early stage of reaction due to the enhanced intensity of electric field between dielectric particles. In (a) of FIG. 6, selectivities of C2 compounds such as ethylene and acetylene were far higher in the packed-bed tests than those in the blank test. In contrast, the selectivity for ethane in the blank test was shown to be higher than those of packed-bed tests. In terms of yield, the unsaturated C2 compounds in the packed-bed tests were produced more than those in the blank test as shown in (b) of FIG. 6. Molar balances on hydrogen and carbon in each test were calculated in Table 3. Due to the high initial activity, significant amount of coke was generated and a few of carbon balances were measured less than 100%.

TABLE 3

| Sample | Blank | α-$Al_2O_3$ | | | sea sand | | | KIT-6 | | |
|---|---|---|---|---|---|---|---|---|---|---|
| Size | — | S | M | L | S | M | L | S | M | L |
| TOS 60 min | | | | | | | | | | |
| CB (%) [a] | 94.22 | 98.15 | 82.70 | 86,68 | 79.97 | 75.02 | 81.10 | 96.84 | 75.86 | 85.32 |
| HB (%) [b] | 97.01 | 98.57 | 93.51 | 93.65 | 95.46 | 95.09 | 92.41 | 99.77 | 92.03 | 94.47 |

TABLE 3-continued

| Sample | Blank | α-Al$_2$O$_3$ | | | sea sand | | | KIT-6 | | |
|---|---|---|---|---|---|---|---|---|---|---|
| Size | — | S | M | L | S | M | L | S | M | L |
| | | | | | TOS 300 min | | | | | |
| CB (%) [a] | 93.50 | 94.00 | 95.44 | 95.89 | 99.12 | 98.09 | 90.61 | 98.71 | 97.49 | 94.12 |
| HB (%) [b] | 96.09 | 93.33 | 95.11 | 97.19 | 100.00 | 99.79 | 97.43 | 99.06 | 98.77 | 97.14 |

[a] Carbon Balance (CB) (%) = $\dfrac{\text{Moles of CH}_4 \text{ not converted} + \sum(x \times \text{Moles of C}_2\text{H}_y \text{ produced})}{\text{Moles of CH}_4} \times 100$

[b] Hydrogen Balance (HB) (%) = $\dfrac{4 \times \text{Moles of CH}_4 \text{ not converted} + 2 \times \text{Moles of H}_2 \text{ produced} + \sum(y \times \text{Moles of C}_2\text{H}_y \text{ produced})}{4 \times \text{Moles of CH}_4 \text{ in the feed}} \times 100$ It was interesting to find that the conversion seemed to have its maximum when the middle-sized particles (size M) were used, irrespective of materials. As described above, by using the new concept of micro-electrodes between dielectric particles, the threshold electric potential difference between polarized dielectric particles may be estimated by employing a slightly modified calculation method from the original Paschen's law, which may be used to estimate a breakdown voltage between electrodes.

Through experimental observation, the maximum conversion rate of methane may be obtained by packing M particles. The gap distance between M particles was in the range of 4 m to 5 m as shown in FIG. 2 and Table 2.

To evaluate the value of threshold electric potential difference, the value of γ was estimated by applying the modified Paschen's equation and the gap at the maximum conversion rate. Since γ is affected by numerous factors, it is known that it is very difficult to estimate the exact value of γ. In the embodiment, the Paschen's equation was applied to estimate secondary electron emission coefficient, γ, for all employed materials for the reaction. This application was based on experimental observation, particularly methane conversion rate in the plasma bed and each gap distance between the particles. By comparing the results of the packed-bed tests with the blank tests, the increased CH$_4$ conversion rate and product selectivity were observed as shown in this study. The level of conversion rate and selectivity seem to be dependent on reaction conditions, types of materials, applied power, and the like.

1.2. Effects of Micro-Discharge on Performance

Figure 7:
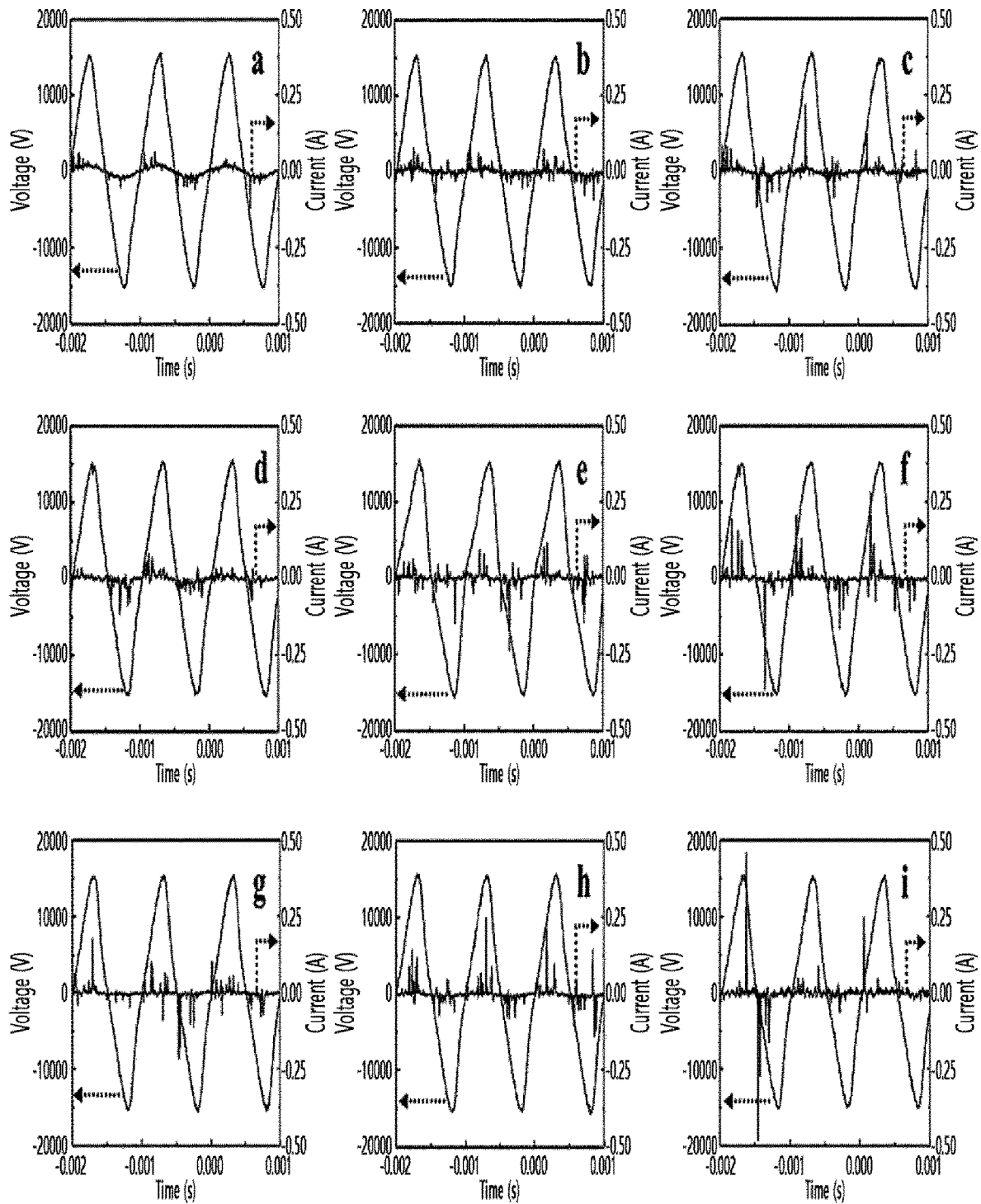
FIG. 7 shows voltage-current profiles of the DBD plasma reactor packed with (a) $\alpha$-$Al_2O_3$ (S), (b) $\alpha$-$Al_2O_3$(M), (c) $\alpha$-$Al_2O_3$(L), (d) sea sand (S), (e) sea sand (M), (f) sea sand (L), (g) KIT-6 (S), (h) KIT-6 (M), and (i) KIT-6 (L).

FIG. 7 shows voltage-current profiles in each packed-bed test. In all cases, several current pulses were observed. These current pulses indicate generation of micro-discharges in the plasma bed.

Table 4 shows average number and average intensity of micro-discharge current pulses per sample measured with voltage-current profile in the packed-bed DBD reactor.

TABLE 4

| Sample | Average number of valid current pulses corresponding to microdischarges per one cycle (—) | Average intensity of microdischarge current pulses (mA) |
|---|---|---|
| Blank | 3.3 | 39.0 |
| α-Al$_2$O$_3$ (S) | 10.0 | 47.5 |
| α-Al$_2$O$_3$ (M) | 13.0 | 54.0 |
| α-Al$_2$O$_3$ (L) | 9.3 | 61.8 |
| sea sand (S) | 12.0 | 48.9 |
| sea sand (M) | 13.0 | 67.5 |
| sea sand (L) | 11.0 | 94.8 |
| KIT-6 (S) | 12.3 | 63.5 |
| KIT-6 (M) | 13.3 | 73.7 |
| KIT-6 (L) | 6.0 | 85.9 |

Referring to FIG. 7 and Table 4, the increased number and intensity of micro-discharges were observed in the cases of packed-bed tests compared with those in the case of blank test.

Also, as shown in Table 4, when large particles were packed, the intensity of micro-discharges increased. As illustrated in FIG. 7, when M particles were used, the number of valid micro-discharges was greatest. Besides the number of contact points, the number of micro-discharges seemed to have strong relation with electric property of dielectric particles such as capacitance, as previously explained. As a result, the maximum conversion rate was observed in the cases of M particles due to the greatest number of micro-discharges with medium intensity.

Table 2 shows discharge power and weight of packed particles. As the particle size decreases, the weight of particles as well as the discharge power seemed to increase in each material (α-Al$_2$O$_3$, sea sand, and KIT-6). The tendency of discharge power in the cases of sea sand samples appeared to be very slightly deviated at L particles, but it may be due to experimental error. It was understood that the increase in bed weight may require more discharge power to polarize the dielectric particles. In addition, Table 2 shows the breakdown voltage in the bed and the threshold electric potential difference between particles. The breakdown voltage was estimated by using Lissajous curves in FIG. 5, and the threshold electric potential difference was computed by using the modified Paschen's equation (Equation 1) to explain the potential difference to initiate streamer or discharge between dielectric particles. The breakdown voltage and the threshold electric potential difference showed their minima in the cases of M particles. This seems highly related to the fact that the conversion showed its maximum in the cases of M particles. The low threshold electric potential difference between the particles seemed to lead to the low breakdown voltage in the entire bed. This reduced breakdown voltage must have facilitated easier formation and a greater number of micro-discharges in the bed as shown in FIG. 7 and Table 4, which resulted in higher converting capability.

1.3. Reaction Pathway Under DBD Plasma

Figure 8:
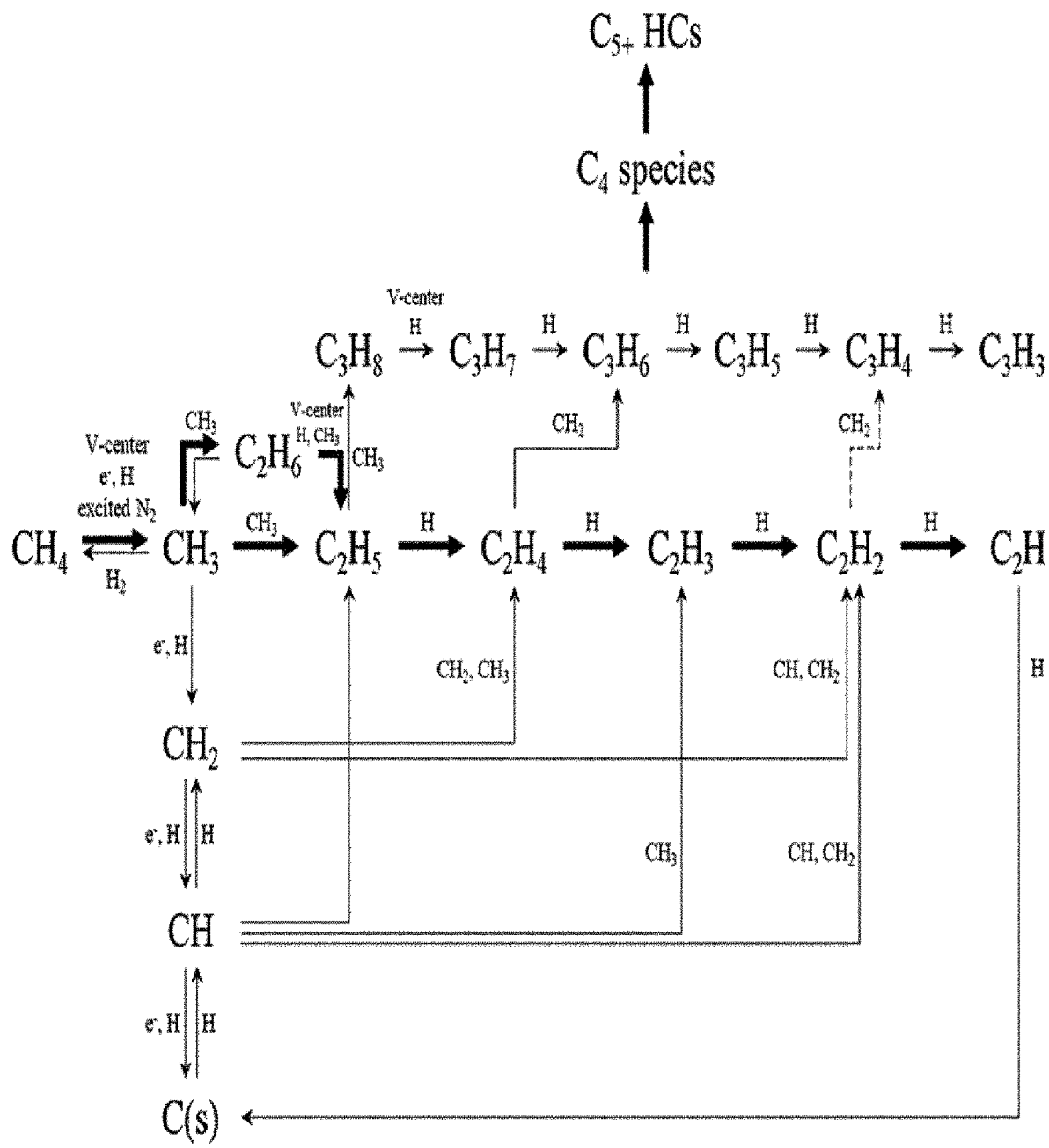
FIG. 8 shows a reaction pathway for describing methane activation, dehydrogenation, coupling, and chain-growth reactions, in which $C_4$ and $C_{5+}$ indicate hydrocarbon molecules having 4 carbon atoms and 5 or more carbon atoms, respectively.

FIG. 8 shows a reaction pathway under the DBD plasma for describing methane activation, dehydrogenation, coupling, and chain-growth reactions.

Regarding unsaturated C2 compounds, the selectivity was shown to increase as the size of particles decreased. The $CH_x$ species dehydrogenated by plasma seemed to have two different routes to be coupled into unsaturated C2 compounds. In the first route, methane is dehydrogenated to a $CH_3$ radical and coupled with another $CH_3$ radical to form $C_2H_6$ (ethane) or $C_2H_5$ species. A further dehydrogenation takes place stepwise to produce $C_2H_4$ (ethylene) and $C_2H_2$ (acetylene). In the second route, the $CH_3$ radical further dehydrogenated to $CH_2$ or CH, which are directly coupled into $C_2H_4$ and $C_2H_2$, respectively.

For S particles, the total selectively for hydrocarbons (selectivity for C2-C4) was found to be the highest. It may result from the highest specific surface area (highest surface to volume ratio for the smallest particles in the cases of nonporous materials such as $\alpha$-$Al_2O_3$ and sea sand particles). This was also valid for highly porous KIT-6 particles. In general, the specific area increases as the size of particle decreases. The specific surface area is proportional to the amount of surface oxygen ion vacancy sites, which are named V-centers and highly related to the generation of methyl radicals ($CH_3$). According to Liu et al., when electronically exited states return to the ground states, energy is emitted in the form of electromagnetic radiation. Such radiation accounts for the ultraviolet to visible emissions of the gas discharge, and the V-center is formed due to the irradiation. The methyl radicals may be formed by interaction with the V-center and methane. According to Ozin et al., the V-center photoactivated by UV irradiation plays a role to dehydrogenate alkane through hydrogen abstraction, and a further dehydrogenation may facilitate the formation of unsaturated forms of hydrocarbons from saturated (i.e., formation of ethylene from ethane). The effect of V-center seems very similar to a catalyst. However, the V-center is thought to be an initiator generating radicals rather than a traditional catalyst.

Besides, the decreased fraction of void space due to the small size particles turned out to be a denser environment and a higher pressure. Under the more compressed condition, the number of effective collisions between intermediate radicals seemed to be increased. In consideration of very short lifetimes of radicals, the small gap distance might have helped the increase in the number of effective collisions avoiding termination without chain-growth.

As a result, the selectivity for unsaturated hydrocarbons and the total hydrocarbon selectivity in the case of S particles were found to be the highest among the 3 different sizes (S, M, and L) regardless of the type of material ($\alpha$-$Al_2O_3$, sea sand, and KIT-6). This was also valid for either practically nonporous or highly porous material.

As a result of observing the phenomenon in the case of the small size particles, the present inventors have found that the dehydrogenated species such as $CH_2$ and CH had higher probability to collide with each other and with their types, and be subsequently coupled into unsaturated C2 compounds. In contrast, if the size of particles was large (L) and the space between particles was also large, the dehydrogenation seemed to occur more frequently than the coupling, which resulted in additional carbon deposition. The increased amount of carbon deposition due to the dehydrogenation seemed to be the result of increased capacitance of large particles. As observed in FIG. 7, the intensity of discharges between L particles was increased and it has been known to increase with capacitance of particles and this led to the amount of charge transferred by an individual micro-discharge was increased, although the number of discharges was decreased due to decreased specific surface area in the cases of L particles.

Due to the large size, the specific surface area is relatively small compared with smaller particles. This is directly related to the number of V-centers. Because of the relatively small number of V-centers, the amount of ethylene from ethane at V-centers seemed to be smaller than that in the cases of smaller particles. In addition, the radicals had relatively low possibility to collide effectively for coupling. Instead, quite a few methyl radicals seemed to have followed the dehydrogenation route (the second route in the above-described mechanism).

1.4. Analysis Results after Plasma Coupling Reaction

In the mechanism of micro-discharge generation described above, the generated $C_xH_y$ radicals may collide with surfaces of the dielectric particles. Due to these collisions, the radicals seemed to be attached to the surfaces and left to form a carbonaceous deposition, which was observed in the spent samples. According to Table 3, the molar balances on carbon in a few samples were quite lower than 100% at the initial stage (TOS 60 min) comparing to the data of TOS 300 min. These results indicate that this type of carbonaceous deposition seemed to be generated dominantly at the initial stage.

Figure 9:
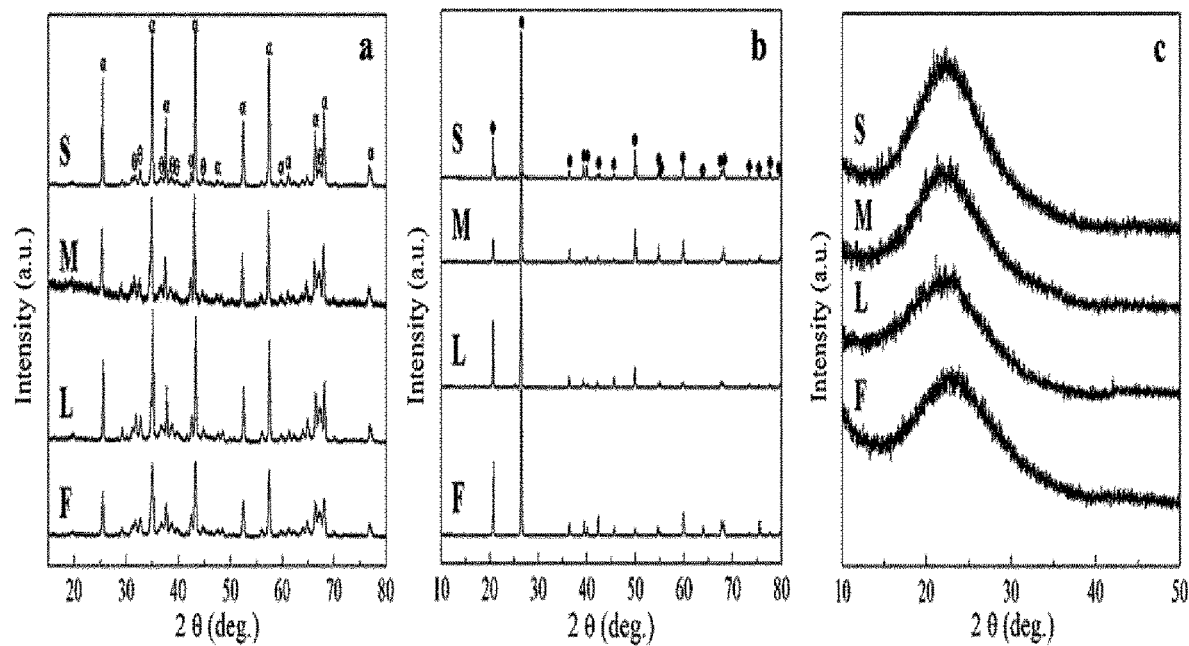
FIG. 9 shows XRD patterns of (a) spent $\alpha\text{-}Al_2O_3$, (b) spent sea sand, and (c) spent KIT-6 samples, in which (S), (M), and (L) respectively indicate sizes of the samples, (F) indicates a fresh sample not used, and $\alpha$, $\theta$, and . are peaks of $\alpha\text{-}Al_2O_3$, $\theta\text{-}Al_2O_3$, and quartz, respectively.
Figure 10:
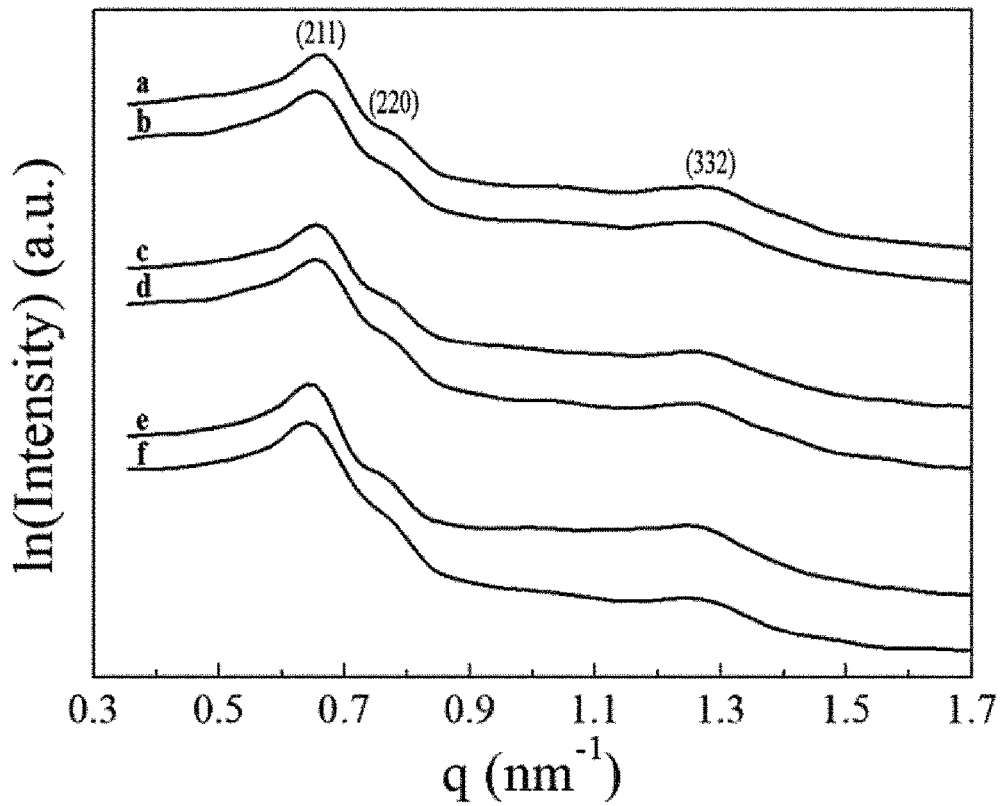
FIG. 10 shows small angle X-ray scattering (SAXS) pattern of (a-b) fresh & spent KIT-6 (S), (c-d) fresh & spent KIT-6 (M), and (e-f) fresh & spent KIT-6 (L).

FIG. 9 shows results of wide angle X-ray diffraction spectroscopy (WAXRD) for spent samples and original fresh samples (not size-controlled). The alumina samples in (a) of FIG. 9 showed that the most dominant phase in the original fresh sample (F) was $\alpha$-phase, but a small fraction of 0-phase was also detected in all the samples. In (b) of FIG. 9, the quartz phase was clearly seen in the fresh and the spent samples. The XRD result in (c) of FIG. 9 showed that all the fresh and spent KIT-6 samples were found amorphous. As shown herein, the phase and the crystallinity of each sample (alumina and sea sand samples) did not change after the plasma coupling reaction. Regarding the KIT-6, the SAXS experiment was utilized to verify the structural stability after the reaction. All the fresh samples showed highly ordered mesoporous structure known as Ia3d bicontinuous phase (a, c, and e of FIG. 10). After the plasma coupling reaction, they successively retained their highly ordered structure, and the spectrum of each spent sample (b, d, and f) showed no significant alternations. The spectrum intensity of spent KIT-6 (L) seemed to be a little bit weakened possibly due to carbon deposition.

Figure 11:
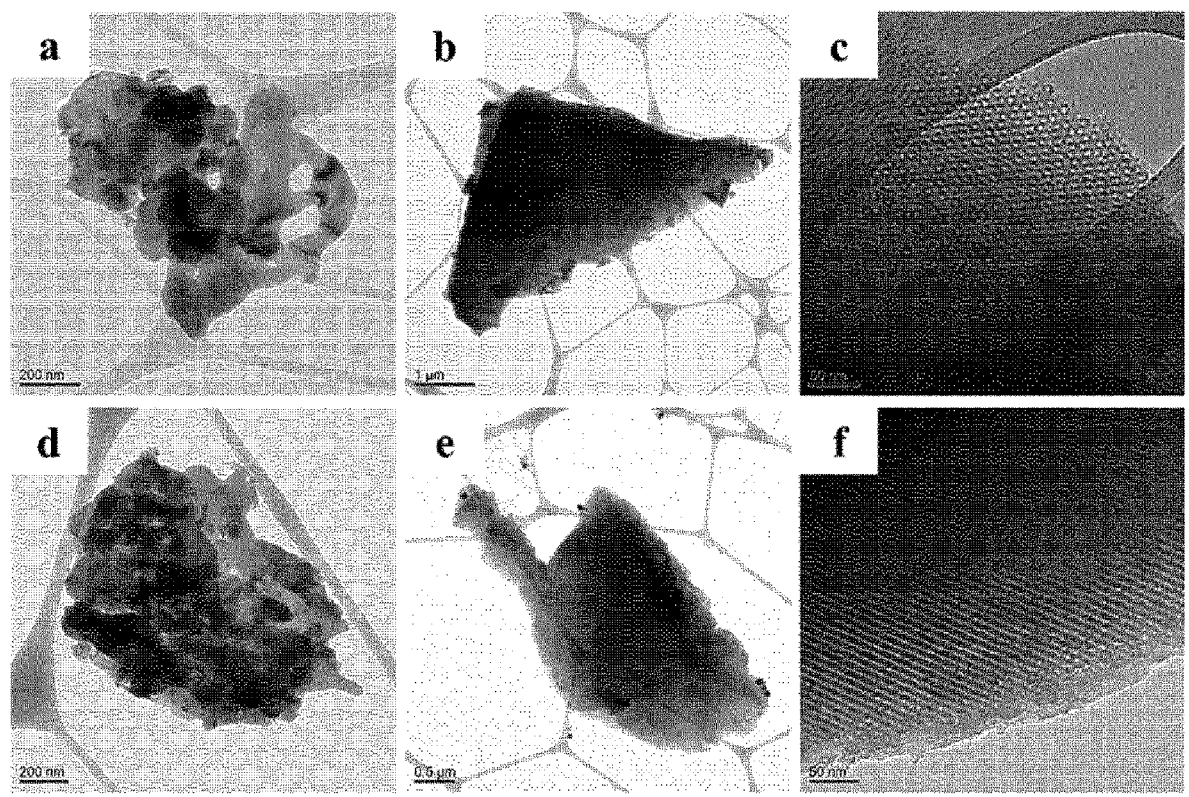
FIG. 11 shows transmission electron microscope (TEM) images of (a) fresh $\alpha\text{-}Al_2O_3$, (b) fresh sea sand, (c) fresh KIT-6, (d) spent $\alpha\text{-}Al_2O_3$, (e) spent sea sand, and (f) spent KIT-6.
Figure 12:
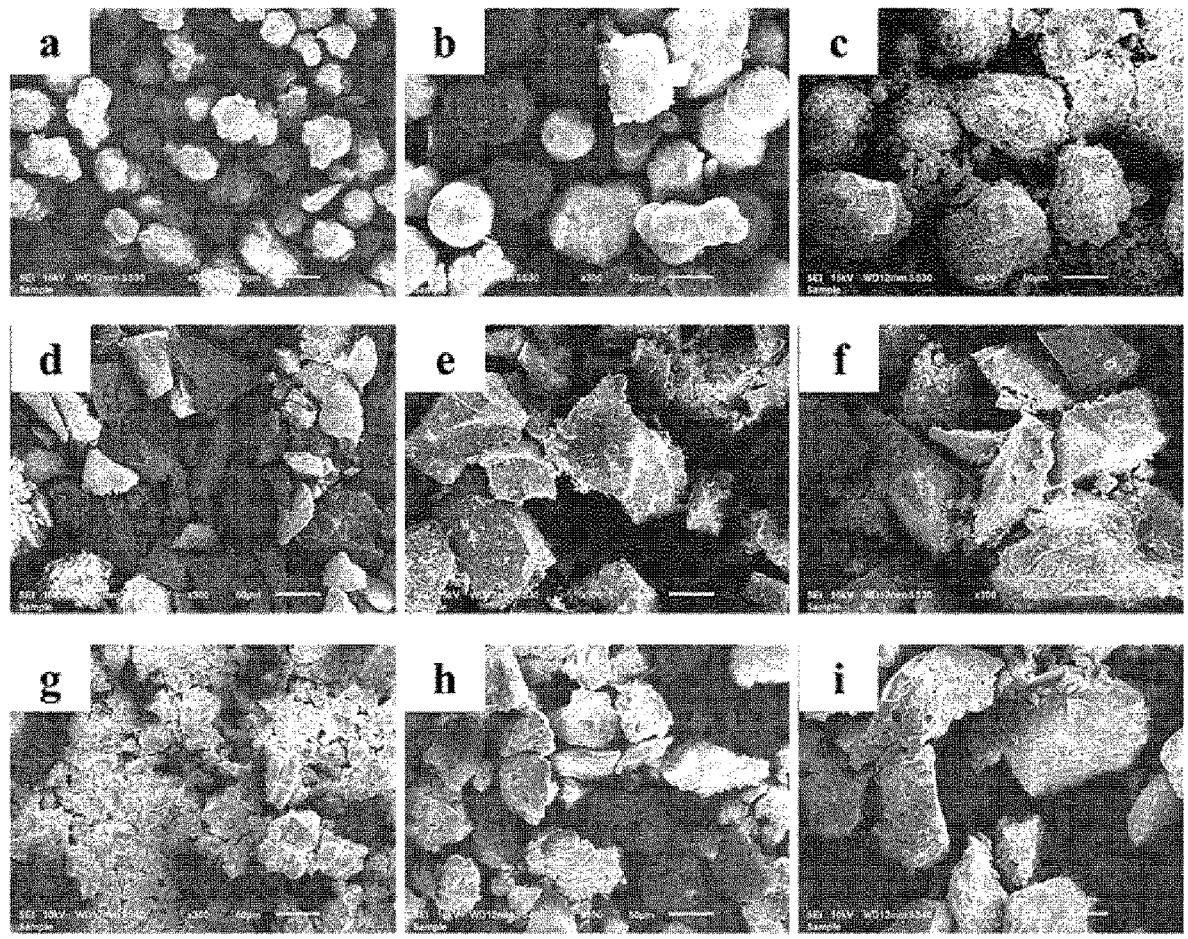
FIG. 12 shows SEM images of (a) spent $\alpha\text{-}Al_2O_3$ (S), (b) spent $\alpha\text{-}Al_2O_3$ (M), (c) spent $\alpha\text{-}Al_2O_3$(L), (d) spent sea sand (S), (e) spent sea sand (M), (f) spent sea sand (L), (g) spent KIT-6 (S), (h) spent KIT-6 (M), and (i) spent KIT-6 (L).
Figure 13:
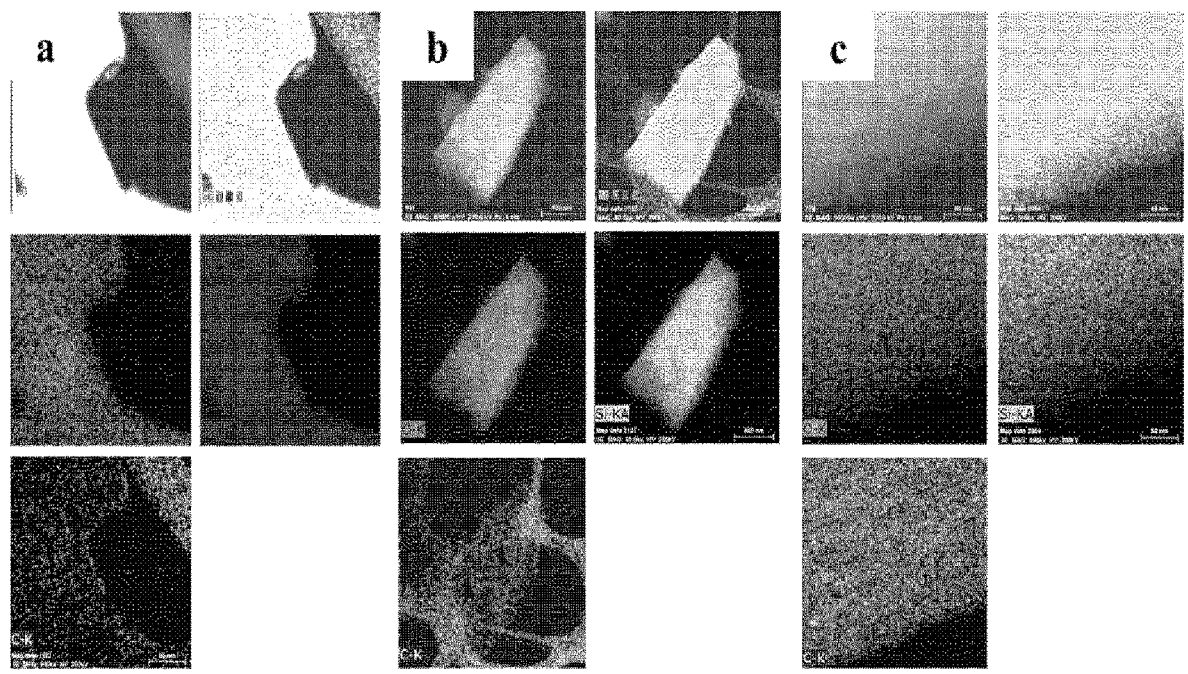
FIG. 13 shows TEM image analysis results of (a) spent $\alpha\text{-}Al_2O_3$, (b) spent sea sand, and (c) spent KIT-6 by EDS.

FIG. 11 shows transmission electron microscope (TEM) images of fresh samples (a to c) and spent samples (d to f). The structural changes were barely observed in the spent samples. In FIG. 12, the particle surface of each spent sample was observed by the SEM images. The changes on the surface of spent samples could be observed and the amount of deposition seemed to be increased as the particle size increased, although the deposited elements such as carbon were hardly identified with these images. FIG. 13 shows the results of TEM imaging analyses with EDS of spent samples. In the cases of spent $\alpha$-$Al_2O_3$ (a) and spent sea sand (b), the carbon deposition on the surface did not seem to be significant, whereas in the case of the spent KIT-6 (c), a significant amount of carbon was observed on the spent KIT-6.

Figure 14:
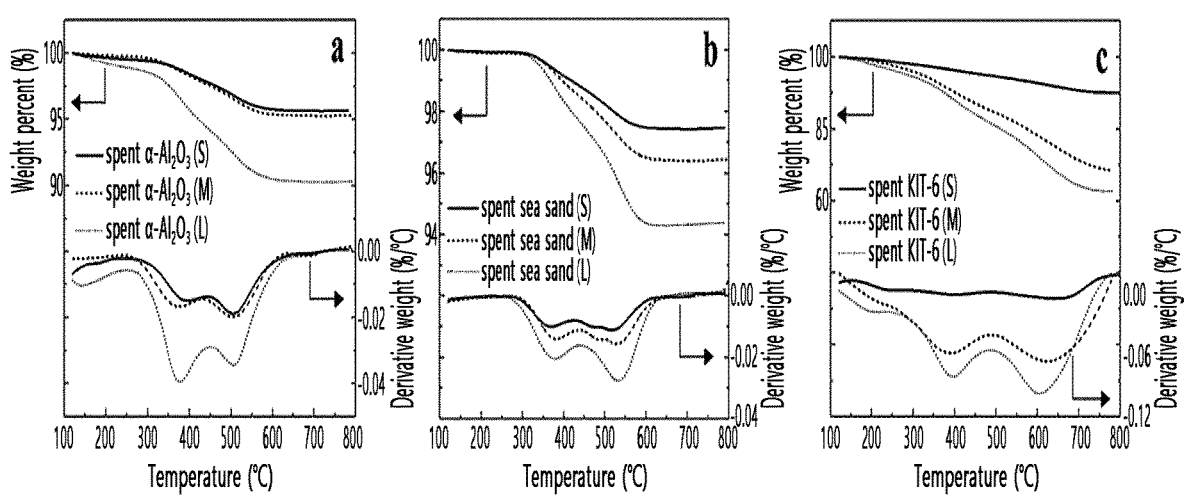
FIG. 14 shows TG/DTA results of (a) spent $\alpha\text{-}Al_2O_3$, (b) spent sea sand, and (c) spent KIT-6.

To assess the carbon deposition, thermogravimetric analysis (TGA) and differential thermal analysis (DTA) were conducted for the spent samples. As shown in FIG. 14 and Table 5 (TG/DTA results of spent $\alpha$-$Al_2O_3$, spent sea sand, and spent KIT-6 samples), the amount of carbon deposition was increased as the size of particles increased. It was understood that the amount of carbon deposition was increased since the increased intensity of micro-discharges for large particles accelerated dehydrogenation.

As shown in the result of TG/DTA, two major peaks were observed at around 400° C. and at a temperature of 500 to 600° C. indicating two different carbon species were deposited. From the XRD results, most of the carbon species were found amorphous, and may be easily removed through traditional oxidation treatments or plasma irradiation techniques. Particularly, the amount of coke in the highly porous KIT-6 was significantly greater than those in the spent $\alpha$-$Al_2O_3$ and sea sand samples. This was possibly due to the fact that the carbon species might have grown into the numerous pores of KIT-6 samples as the reaction proceeded.

TABLE 5

|  | Weight loss (%) | lower DTA peak (° C.) | higher DTA peak (° C.) |
| --- | --- | --- | --- |
| $\alpha$-$Al_2O_3$ (S) | 4.32 | 387 | 505 |
| $\alpha$-$Al_2O_3$ (M) | 4.67 | 373 | 506 |
| $\alpha$-$Al_2O_3$ (L) | 9.67 | 378 | 506 |
| sea sand (S) | 2.52 | 376 | 518 |
| sea sand (M) | 3.54 | 379 | 529 |
| sea sand (L) | 5.61 | 379 | 533 |
| KIT-6 (S) | 9.95 | 396 | 648 |
| KIT-6 (M) | 31.3 | 395 | 624 |
| KIT-6 (L) | 37.3 | 398 | 606 |

Figure 15:
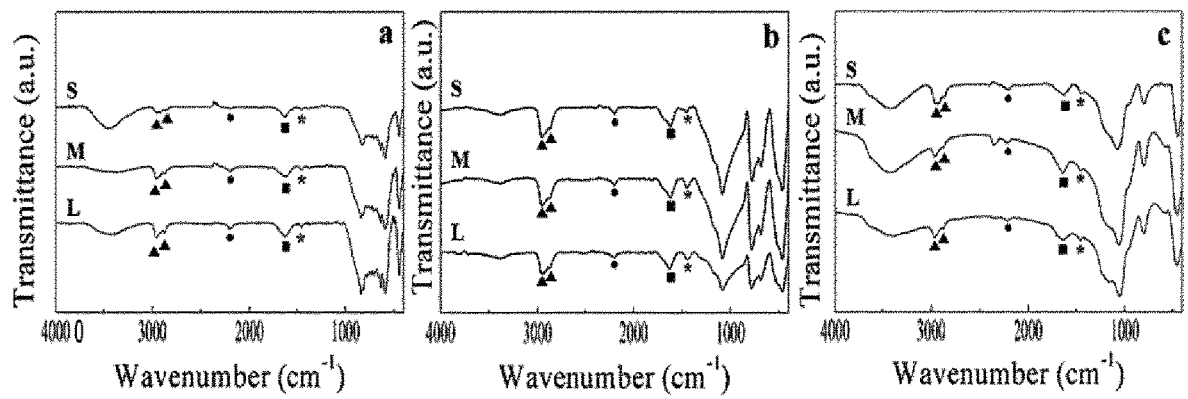
FIG. 15 shows FT-IR spectra of (a) $\alpha\text{-}Al_2O_3$, (b) sea sand, and (c) KIT-6. ▲, •, ■, and * indicates $CH_3$ stretch vibration mode, C≡C stretching mode or cyano group, C=C stretching mode, and asymmetric C—H bending mode of methylene group in a long aliphatic chain.

FIG. 15 shows the result of FT-IR observation. The similar species of carbon were detected in all the spent samples. At 2850 and 3000 $cm^{-1}$, a $CH_3$ stretch vibration mode was observed. The peak at 2200 $cm^{-1}$ may be assigned to the carbon-carbon triple bond stretching mode, or cyano group (—CN) due to chemical reaction between $CH_4$ and $N_2$. The peaks at 1640 $cm^{-1}$ and 1463 $cm^{-1}$ may be ascribed to the carbon-carbon double bond stretching mode, and the asymmetric C—H bending mode of methylene group in a long aliphatic chain, respectively. Considering all these features, the carbon species in the FT-IR spectra could be classified as carbon deposition having long-chain hydrocarbons.

Preparation Example 2

Figure 1:
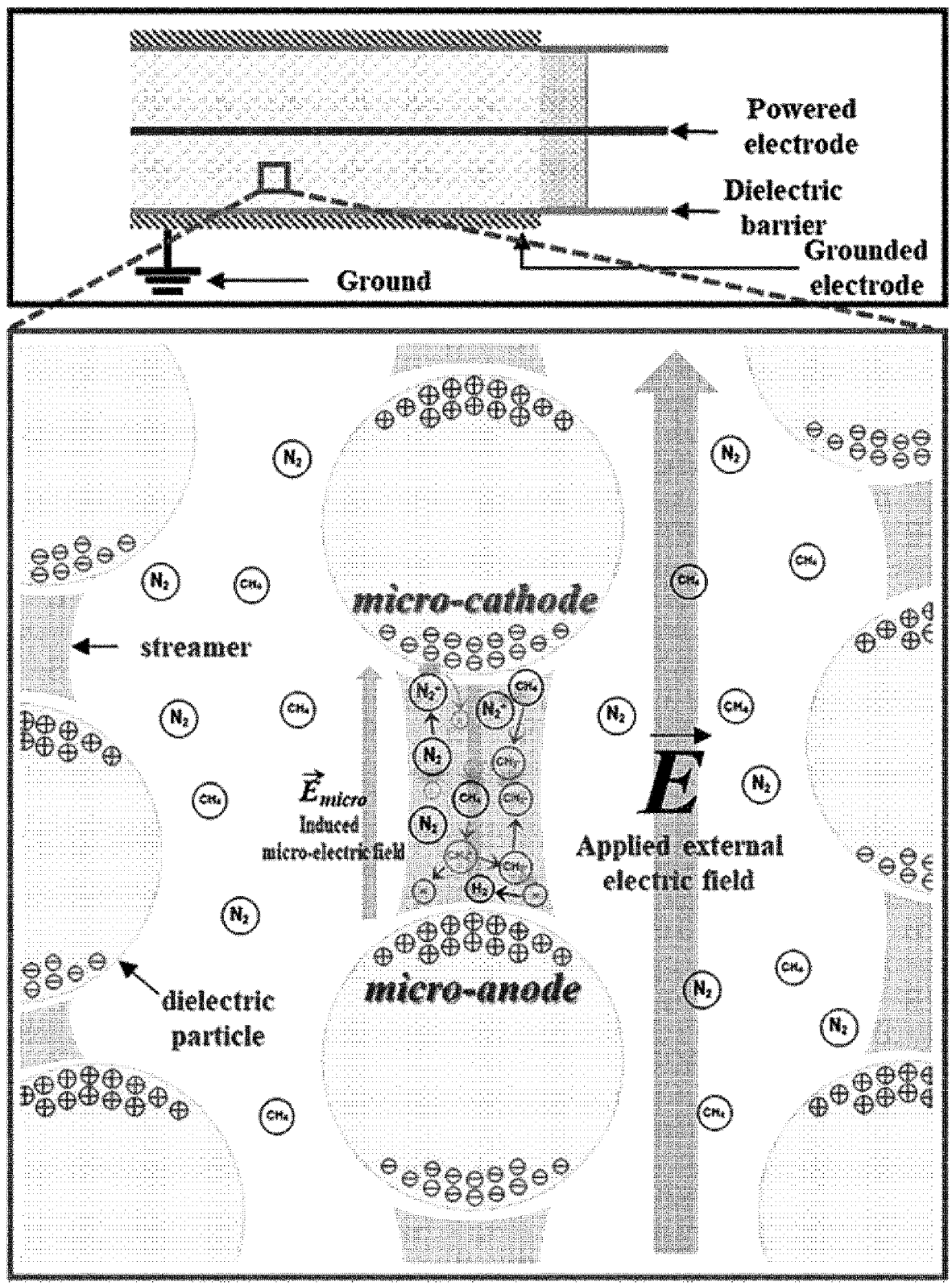
FIG. 1 is a schematic conceptual diagram illustrating streamers and reactive intermediates between dielectric particles by an induced microelectric field.

An experimental device of dielectric barrier discharge plasma is shown in FIG. 1. As a plasma reactor, an alumina tube having a length of 700 mm, an external diameter of 10 mm, and an internal diameter of 6 mm was used. This alumina tube served as a dielectric barrier. A stainless steel rod having a diameter of 3 mm was used as a high-voltage electrode, and a steel wire having a thickness of 0.5 mm and wound on the alumina tube in a spring form by 150 mm was used as a ground electrode. An AC power supply (0 to 220 V, 60 to 1000 Hz) was connected to a transformer (0 to 20 kV, 1000 Hz), and an oscilloscope and a high-voltage probe were used to measure voltage. In addition, a 1 µF capacitor was connected to the reactor in series, and an amount of charge was measured by measuring a potential difference between both ends of the capacitor.

The reactants were quantitatively analyzed by using an on-line gas chromatography (6500GC Young Lin Instrument Co., Korea). The thermal conductivity detector (TCD) and the flame ionization detector (FID) were used as detectors, and a Porapak-N, Molecular Sieve 13× column was used for the TCD and a methanizer was used for the FID. $H_2$, $N_2$, and $CH_4$ were detected using the TCD, and $CH_4$, $C_2H_2$, $C_2H_4$, $C_2H_6$, and C3 and C4 hydrocarbons were detected using the FID.

Preparation Example 3: Porous Silica KIT-6 Used in Paced Layer

Mesoporous silica KIT-6 was prepared according to the following process. A copolymer pluronic p-123 was used as a structure inducer to form a three-dimensional structure of the mesoporous silica KIT-6. This copolymer forms a micelles in an aqueous solution and serves to form a mesoporous silica structure through interactions with silicon ions and self-assembly. 6 g of pluronic p-123 was added to an aqueous solution prepared by mixing 217.64 ml of distilled water and 11.16 g of a 37 wt % HCL solution and rapidly stirred at about 35° C. until the pluronic p-123 was completely dissolved. Subsequently, 6 g of n-butanol was added to the prepared mixed solution and further stirred for 2 hours while maintaining the temperature to form an Ia3d structure that is an intrinsic structure of KIT-6. Thereafter, 12.77 g of tetraethoxysilane (TEOS) was added dropwise to the mixed solution while stirring and then rapidly stirred at about 35° C. for 24 hours. After this process, a solution in which white silica deposits are formed was added to a polypropylene container and transferred to a hydrothermal synthesis device, and hydrothermal synthesis was performed at about 100° C. for one day without stirring. Then, a washing process was performed to remove solvents remaining in the reaction solution. After washing with distilled water for 30 minutes, washing with ethanol was performed three times to remove the pluronic p-123 and remaining impurities. Then, the resultant was dried in an oven at 110° C. for one day. The dried white silica powder was heated to 400° C. at a heating rate of 2° C./min and maintained for 3 hours, and then the powder was heated to 550° C. at a heating rate of 1° C./min and maintained for 5 hours to perform a calcination process. After the calcination was completed, the white silica powder was separated in terms of particle size of 100-150 μm by using sieves.

Example 2: Oxygen-free Methane Coupling Reaction with Packing Material

Figure 16:
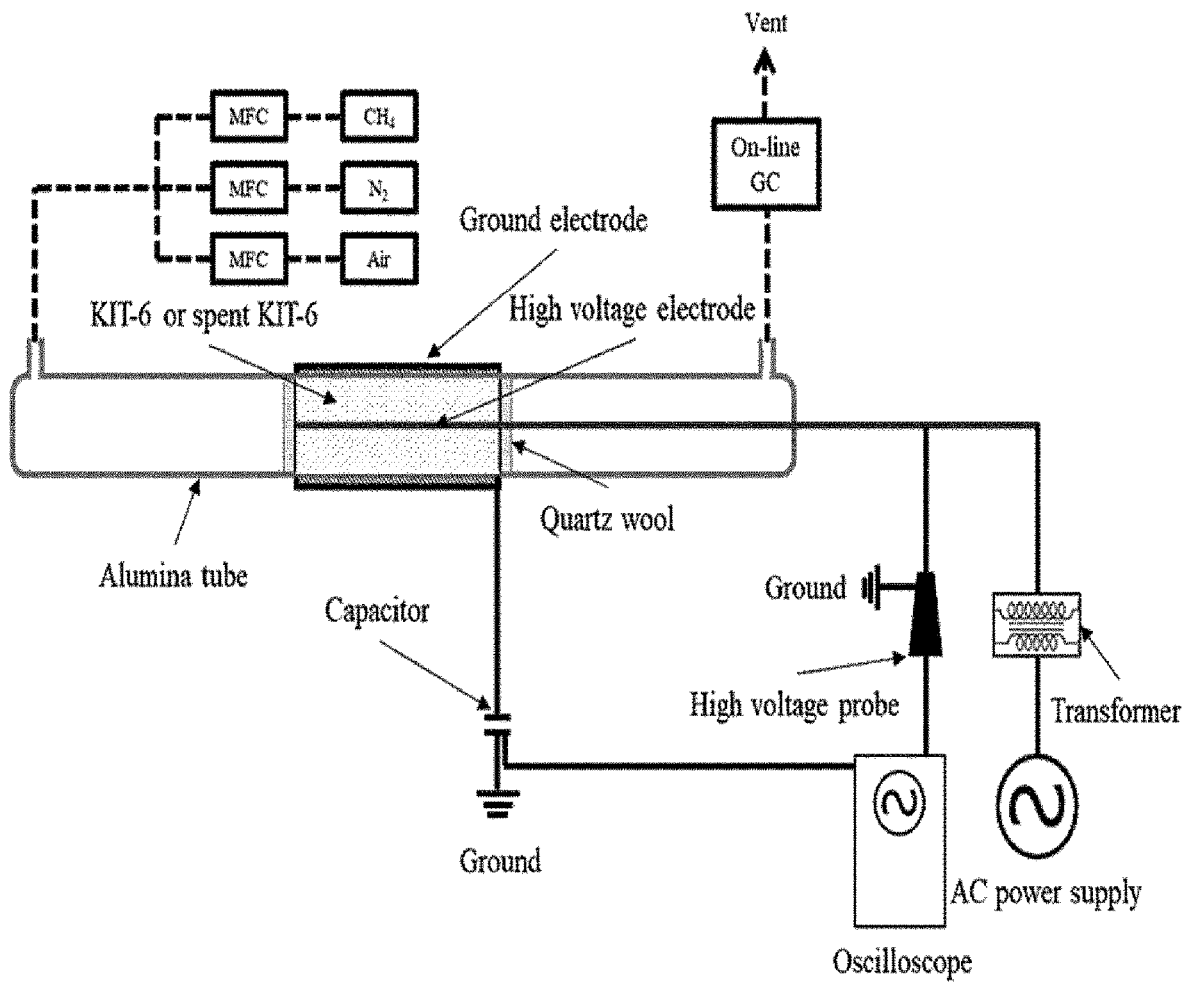
FIG. 16 is a schematic diagram of a dielectric barrier discharge plasma reactor.

The dielectric barrier discharge plasma reactor (FIG. 16) prepared in Preparation Example 2 was used. Plasma was generated in an alumina tube between the high-voltage electrode and the ground electrode wound by a length of 150 mm. The alumina tube was packed with the packing material prepared according to Preparation Example 2 except for a volume of 3.181 cm$^3$ occupied by the high-voltage electrode. The oxygen-free methane coupling reaction was performed at room temperature and atmospheric pressure. NFC for $CH_4$ and $N_2$ was connected to the DBD plasma bed to inject $CH_4$ and $N_2$ in a ratio of 1:1, and the reaction was performed at a gas hourly space velocity (GHSV) of 2,500 mL·g$^{-1}$·h$^{-1}$. The experiment was performed while maintaining a voltage of 15 kV and a frequency of 1000 Hz. The oxygen-free methane coupling reaction was performed for 1000 minutes.

Products were analyzed at 20 minutes after the reaction was initiated by an online gas chromatography and analysis was repeated at intervals of 40 minutes.

Example 3: Regeneration Using Low Temperature Plasma

After Example 2 described above, a regeneration reaction of the deactivated packing material was performed by using the DBD plasma. The configuration of the plasma reactor was the same as that shown in FIG. 16, and the experiment was performed by packing the alumina tube with the packing material in the same volume as that of Example 2. In addition, the regeneration reaction was performed at room temperature and atmospheric pressure. An NFC was connected to the DBD plasma bed to inject Air into the DBD plasma bed, and the reaction was performed at a gas hourly space velocity (GHSV) of 1,250 mL·g$^{-1}$·h$^{-1}$. The experiment was performed while maintaining a voltage of 15 kV and a frequency of 1000 Hz. The regeneration reaction was performed for 720 minutes.

Comparative Example 1: Regeneration by Heat Treatment

After the Example 2 described above, the deactivated packing material was heated to 700° C. in a muffle furnace at a heating rate of 5° C./m while flowing air at a flow rate of 50 sccm and maintained for 5 hours.

Figure 17:
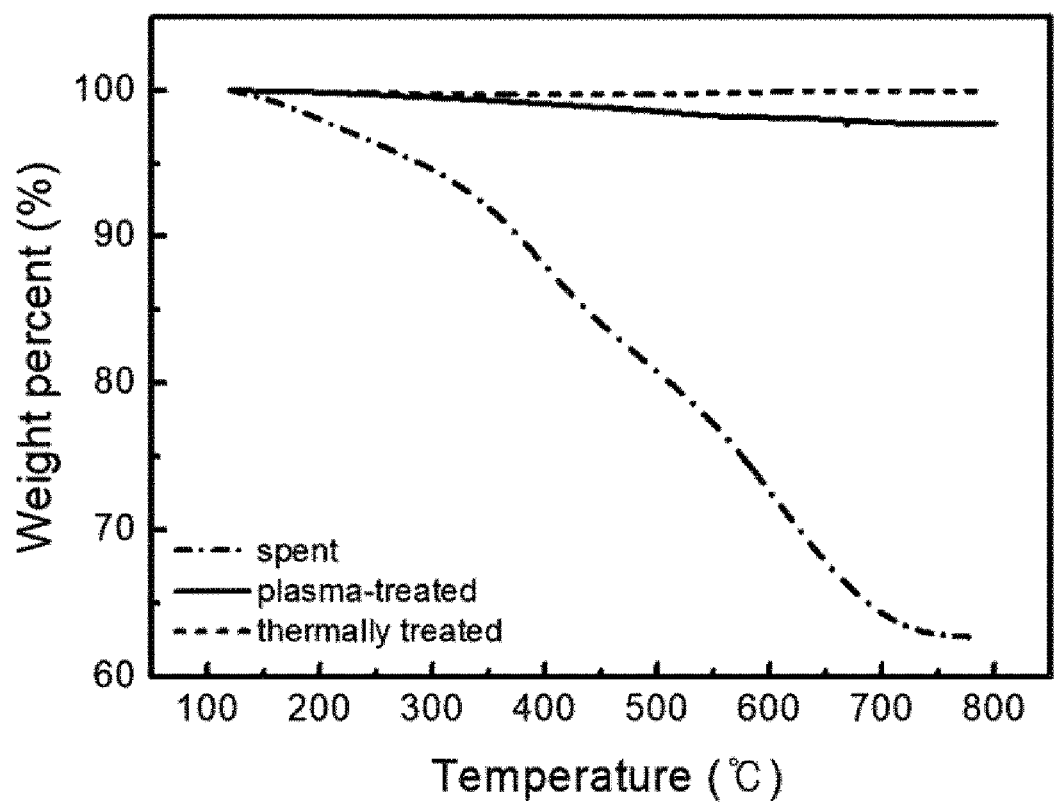
FIG. 17 shows TGA results of packing materials collected after Example 2, Example 3, and Comparative Example 1.

Example 4: TGA for Deactivated Packing Material and Regenerated Packing Material The packing materials collected after Example 2, Example 3, and Comparative Example 1 were subjected to TGA, and results are shown in FIG. 17, and weight losses, total amounts of coke, and removal rates thereof are summarized in Table 6. Comparing the total amounts of coke between Example 3 and Comparative Example 1, it was confirmed that a difference of the removal rate between Example 3 and Comparative Example 1 was only 3.23% p although the effect of Example 3 was not clearly identified. This indicates that most of coke was removed according to Comparative Example 1, and coke was removed according to Example 3 at the same level.

TABLE 6

| | Weight loss (%) | Total amount of coke (amount of coke per weight of packing material (g-coke/g-$SiO_2$)) | Removal rate$^a$ (%) | Note |
|---|---|---|---|---|
| Example 2 | 37.32 | 0.60 | — | Amount of coke generated by reaction |
| Example 3 | 2.30 | 0.02 | 96.67 | Amount of coke removed by plasma |
| Comparative Example 1 | 0.06 | 0.0006 | 99.90 | Amount of coke removed by heat treatment |

$^a$Removed amount of coke/total amount of coke according to Example 1

Example 5: Confirmation of Removal of Coke by FT-IR

Figure 18:
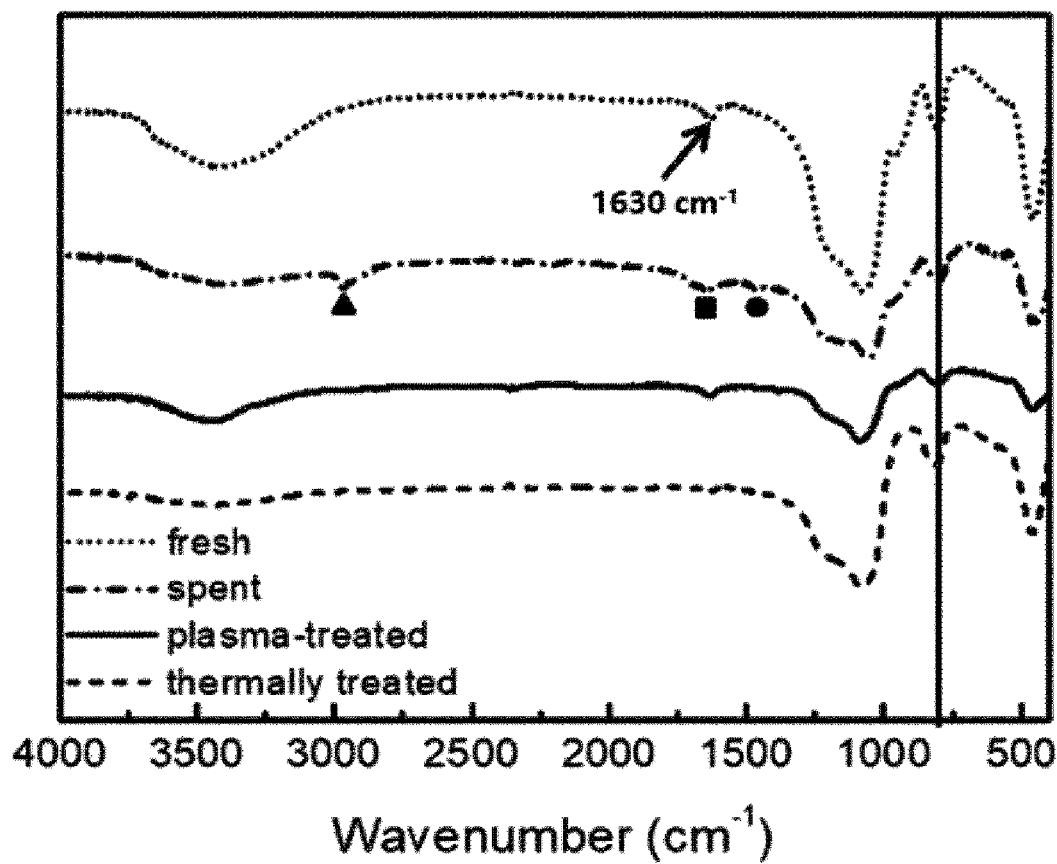
FIG. 18 shows FR-IR analysis results of packing materials collected after Preparation Example 3, Example 2, Example 3, and Comparative Example 1.

After Preparation Example 3, Example 2, Example 3, and Comparative Example 1, collected packing materials were subjected to Fourier-transform infrared spectroscopy (FT-IR) analysis, and results are shown in FIG. 18. In the case of Example 2, three types of vibration modes were identified. ▲ indicates a $CH_3$ stretch vibration mode, ■ indicates an asymmetrical C=C stretching mode, and • indicates an asymmetrical C—H bending mode of methylene groups in a long aliphatic chain. On the contrary, in Example 3 and Comparative Example 1, these vibration modes were not observed. Although peaks were observed nearby at 1630 cm$^{-1}$ in the cases of Preparation Example 3, Example 3, and Comparative Example 1, it is an O—H bending mode which was not adsorbed and not detached therefrom even after being sufficiently dried.

In addition, while Si—O—Si bonding was observed at 806 cm$^{-1}$ in the cases of Preparation Example 3, Example 2, and Example 3, it was observed at 816 cm$^{-1}$ in the case of Comparative Example 1.

Example 6: Analysis of Position of Coke Using TEM Image

Figure 19:
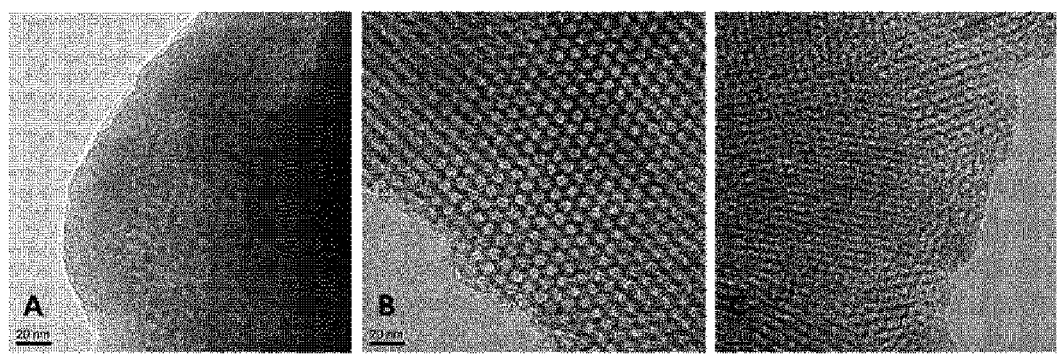
FIG. 19 shows TEM image analysis results of packing materials collected after Example 2, Example 3, and Comparative Example 1.

The packing materials collected after Example 2, Example 3, and Comparative Example 1 were subjected to TEM analysis, and results are shown in FIG. 19. A TEM image of the packing material collected after Example 2 was shown in FIG. 19-A, a TEM image of the packing material collected after Example 3 was shown in FIG. 19-B, and a TEM image of the packing material collected after Comparative Example 1 was shown in FIG. 19-C. Although coke was stacked on the surface of the packing material through FIG. 19-A, it may be confirmed that large amounts of coke were removed from the stack structures in the cases of FIGS. 19-B and 19-C.

Regarding FIG. 19, energy-dispersive X-ray (EDX) mapping analysis results are shown in Table 7. Referring to Table 7, a mass percent of carbon was reduced by 19.12% p in the case of FIG. 19-B, and the mass percent of carbon was reduced by 31.01% p in the case of FIG. 19-C. This indicates that coke may be effectively removed from the deactivated packing material by using the low temperature DBD plasma and the muffle furnace.

TABLE 7

| | Mass percent (%) | | |
|---|---|---|---|
| | C | O | Si |
| FIG. 19-A (Example 2) | 60.60 | 12.98 | 26.42 |
| FIG. 19-B (Example 3) | 41.48 | 25.73 | 32.79 |
| FIG. 19-C (Comparative Example 1) | 29.59 | 30.23 | 40.18 |

Example 7: Structural Stability by XRD Characteristic Analysis

Figure 20:
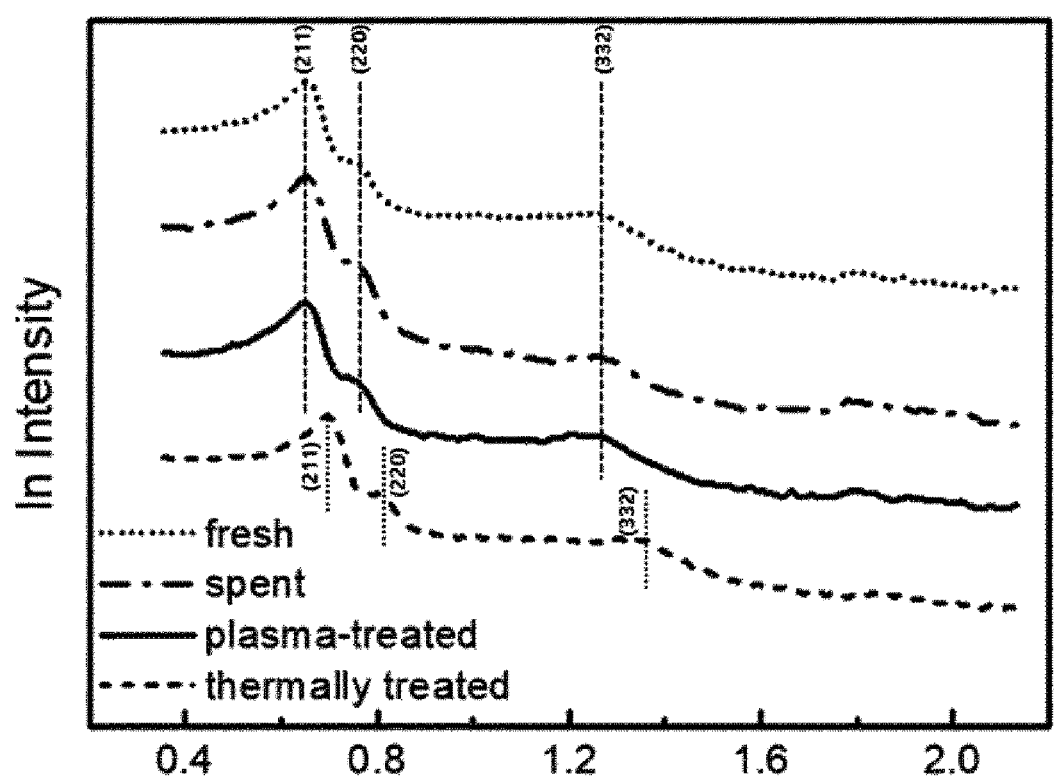
FIG. 20 shows small angle X-ray scattering (SAXS) analysis results of packing materials collected after Preparation Example 3, Example 2, Example 3, and Comparative Example 1.

The packing materials collected after Preparation Example 3, Example 2, Example 3, and Comparative Example 1 were subjected to small angle X-ray scattering (SAXS) analysis, and results are shown in FIG. 20. It was confirmed that SAXS graphs of the packing materials collected after Example 2 and Example 3 were identical to the SAXS graph of the fresh packing material. It was also confirmed that the oxygen-free methane coupling reaction using the DBD plasma and the regeneration reaction of the packing material did not affect structural stability of the packing material. On the contrary, it was confirmed that the SAXS graph of the packing material collected after Comparative Example 1 was different from the SAXS graph of the fresh packing material. Therefore, it was confirmed that the regeneration reaction using the muffle furnace affected the structural stability of the packing material.

Example 8: Structural Stability by BET Characteristic Analysis

Table 8 shows BET surface areas, pore volumes, and pore sizes according to Preparation Example 3, Example 3, and Comparative Example 1. Referring to Table 8, it was difficult to maintain the structural stability in the case of the regeneration reaction using the muffle furnace when compared with the case of the regeneration reaction using the plasma.

TABLE 8

| | BET Surface Area (m$^2$/g) | Pore Volume (cm$^3$/g) | Pore Size (nm) |
|---|---|---|---|
| Preparation Example 3 | 774.92 | 1.12 | 6.40 |
| Example 3 | 749.04 | 0.91 | 6.05 |
| Comparative Example 1 | 546.68 | 0.76 | 6.01 |

Example 9: Reaction Performance of Packing Material for Plasma Regeneration

Fresh KIT-6 and the packing material collected after Example 3 were subjected to reaction performance tests and results at TOS 60 min are shown in Table 9. Reaction conditions are the same as those in Example 2. When reaction performance of Fresh KIT-6, as the packing material before the reaction, was compared with that of Example 3, the methane conversion rate was slightly increased but the selectivity for C2 hydrocarbons was slightly decreased. It is considered that a small amount of unremoved coke remaining on the surface of KIT-6 as a coating layer affected the performance. However, the overall yield of light hydrocarbons was maintained at a similar level to that of Fresh KIT-6, and it is considered that plasma-regenerated KIT-6 may be used in a plasma bed for coupling of methane.

TABLE 9

| | CH$_4$ Conversion (%) | Selectivity (%) | | | | |
|---|---|---|---|---|---|---|
| | | Acetylene | Ethylene | Ethane | C3 hydrocarbons | C4 hydrocarbons |
| Fresh KIT-6 | 41.80 | 15.53 | 6.39 | 21.64 | 10.74 | 11.54 |
| Plasma-treated KIT-6 | 48.85 | 10.15 | 3.81 | 16.13 | 10.57 | 9.08 |

The invention claimed is:

1. A dielectric barrier discharge (DBD) plasma reactor comprising:
   a tube having a first end and a second end;
   a gas inlet coupled to the first end;
   a gas outlet coupled to the second;
   dielectric particles that are disposed in the tube to form a plasma bed, the dielectric particles being packed in a discharge zone of the tube, the dielectric particles being packed between layers of supporting material,
   wherein the dielectric particles having diameter of 53 μm to 100 μm,
   wherein the DBD plasma reactor is a reactor for non-oxidative coupling of methane designed to cause a non-oxidative coupling reaction of methane, wherein a mean value of a gap distance between the dielectric particles in the bed which are polarized by external electric field is 4 μm to 5 μm.

2. The DBD plasma reactor of claim 1, wherein the gap distance between the dielectric particles in the bed is determined by particle size.

3. The DBD plasma reactor of claim 1, wherein the gap distance between the dielectric particles is selected to obtain desired methane conversion rate and C2 selectivity.

4. The DBD plasma reactor of claim 1, wherein C—H bonds are activated without additional thermal energy and oxidant molecules to produce methyl radicals and directly produce C2-C4 light hydrocarbons.

5. The DBD plasma reactor of claim 1, wherein a particle size of the dielectric particles is selected to inhibit formation of coke on the dielectric particles during the reaction or to control timing of removing coke formed on the dielectric particles during the reaction.

6. The DBD plasma reactor of claim 1, wherein the reactor is designed to remove coke formed on the dielectric particles by side reactions by plasma treatment in an oxidizing atmosphere.

7. The DBD plasma reactor of claim 1, wherein the reactor is designed to remove coke inevitably accompanied by side reactions during the reaction occurring in the DBD plasma reactor by using the same type of plasma as that used in the reaction by supplying an oxygen-containing mixture, instead of a reaction mixture, in a regeneration process of removing the coke.

* * * * *